United States Patent
Burckhardt et al.

(10) Patent No.: US 11,535,694 B2
(45) Date of Patent: Dec. 27, 2022

(54) LATENT CURING AGENT AND CURABLE POLYURETHANE COMPOSITION

(71) Applicant: SIKA TECHNOLOGY AG, Baar (CH)

(72) Inventors: Urs Burckhardt, Zürich (CH); Andreas Kramer, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 152 days.

(21) Appl. No.: 16/613,888

(22) PCT Filed: Jun. 19, 2018

(86) PCT No.: PCT/EP2018/066177
§ 371 (c)(1),
(2) Date: Nov. 15, 2019

(87) PCT Pub. No.: WO2018/234267
PCT Pub. Date: Dec. 27, 2018

(65) Prior Publication Data
US 2020/0140599 A1  May 7, 2020

(30) Foreign Application Priority Data
Jun. 19, 2017 (EP) .................................. 17176688

(51) Int. Cl.
| | |
|---|---|
| *C08G 18/32* | (2006.01) |
| *C08G 18/20* | (2006.01) |
| *C07D 413/12* | (2006.01) |
| *C08G 18/48* | (2006.01) |
| *C08G 18/75* | (2006.01) |
| *C08G 18/76* | (2006.01) |
| *C09D 175/08* | (2006.01) |
| *C09J 175/08* | (2006.01) |
| *C09K 3/10* | (2006.01) |

(52) U.S. Cl.
CPC ....... *C08G 18/2081* (2013.01); *C07D 413/12* (2013.01); *C08G 18/3256* (2013.01); *C08G 18/3296* (2013.01); *C08G 18/485* (2013.01); *C08G 18/4812* (2013.01); *C08G 18/4825* (2013.01); *C08G 18/4829* (2013.01); *C08G 18/755* (2013.01); *C08G 18/7621* (2013.01); *C08G 18/7671* (2013.01); *C09D 175/08* (2013.01); *C09J 175/08* (2013.01); *C09K 3/1021* (2013.01); *C09K 2200/065* (2013.01)

(58) Field of Classification Search
CPC .................. C08G 18/3296; C08G 18/3256
See application file for complete search history.

(56) References Cited

U.S. PATENT DOCUMENTS

| | | | |
|---|---|---|---|
| 5,189,176 A | 2/1993 | Blum et al. | |
| 6,103,849 A * | 8/2000 | Squiller | ................ C08G 18/10 528/45 |
| 8,618,237 B2 * | 12/2013 | Booth | ................ C08G 18/3844 528/73 |
| 2015/0111991 A1 | 4/2015 | Kitamura et al. | |

FOREIGN PATENT DOCUMENTS

| | | |
|---|---|---|
| JP | H08-034776 A | 2/1996 |
| JP | H10-226720 A | 8/1998 |
| JP | 2002-194048 A | 7/2002 |
| JP | 2004-107370 A | 4/2004 |
| WO | 2004/013088 A1 | 2/2004 |
| WO | 2010/068736 A2 | 6/2010 |

OTHER PUBLICATIONS

Sep. 12, 2018 Search Report issued in International Patent Application No. PCT/EP2018/066177.
Dec. 24, 2019 International Preliminary Report on Patentability issued in International Patent Application No. PCT/EP2018/066177.

* cited by examiner

*Primary Examiner* — Michael L Leonard
(74) *Attorney, Agent, or Firm* — Oliff PLC

(57) ABSTRACT

A compound of formula (I) having advantageous properties when used as a latent curing agent for compositions containing isocyanate groups, and to compositions containing the compound of formula (I). The compound of formula (I) is odourless, is liquid and has comparatively low viscosity at room temperature and is stable in storage together with isocyanates. It makes possible odourless single-component polyurethane compositions which have good stability in storage, do not produce bubbles when cured in the presence of moisture, and cause no problematic odour emissions, giving a cured elastic material having good mechanical properties, good heat stability, a surprisingly non-adhesive surface and little tendency towards plasticizer migration.

6 Claims, No Drawings

LATENT CURING AGENT AND CURABLE POLYURETHANE COMPOSITION

TECHNICAL FIELD

The invention relates to latent curing agents and to curable polyurethane compositions comprising them, and also to adhesives, sealants and coatings.

STATE OF THE ART

Curable polyurethane compositions which crosslink through reaction of isocyanate groups with hydroxyl groups and/or moisture or water are used in many industrial applications, for example as adhesives, sealants or coatings in the construction and manufacturing industries. When compositions of this kind are used at high humidity and/or elevated temperature, the curing thereof often gives rise to disruptive blisters as a result of carbon dioxide gas released, which is not dissolved or dissipated quickly enough. In order to avoid blistering, it is possible to add chemically blocked amines to the compositions, called latent curing agents, which release amino groups on contact with moisture and are crosslinked rapidly with the isocyanate groups without formation of carbon dioxide. Latent curing agents used are usually compounds having aldimine, ketimine or oxazolidine groups. However, the known latent curing agents are disadvantageous. For instance, they can trigger premature crosslinking reactions and hence lower the storage stability of the compositions and/or accelerate the curing thereof to such a degree as to result in too short an open time and hence too short a working window. Moreover, many of the known latent curing agents, on curing, lead to troublesome immissions caused by highly volatile, intensely odorous, aldehydes or ketones which serve as blocking agents in the latent curing agent and are released through hydrolysis. Latent curing agents having oxazolidine groups differ from those having aldimine or ketimine groups in that their hydrolysis gives rise not just to an amino group but additionally to a hydroxyl group which is likewise isocyanate-reactive. This makes them particularly economical in use, leads to release of smaller amounts of blocking agent on curing and increases the crosslinking density, which is advantageous for coatings in particular. However, they also have drawbacks that greatly restrict their use. The most commercially well-known oxazolidine curing agent Incozol 4 is solid at or a little below room temperature and therefore has to be melted or dissolved in a solvent. Moreover, it has only very limited storability with many isocyanates and releases isobutyraldehyde, which is highly volatile and odorous, on curing. U.S. Pat. No. 5,189,176 describes corresponding oxazolidine curing agents based on 2-ethylhexanal. Although these are liquid at room temperature, they likewise only have very limited storability with isocyanates and lead to very strong odor immissions. Moreover, 2-ethylhexanal is toxic.

Also known are oxazolidine curing agents derived from aromatic aldehydes, for example from JP H08-034776 or JP 2002-194048. These are solid at room temperature and lead to strong odor immissions and in some cases to discoloration.

WO 2004/013088 discloses odorless aldimine curing agents blocked with odorless tertiary aliphatic long-chain and ester-containing aldehydes. Oxazolidine curing agents based on these aldehydes were proposed in WO 2010/068736 for use in hotmelt adhesives. They are storage-stable with all isocyanates and do not cause any odor immissions, but are hydrolyzed only very slowly and are therefore only incompletely incorporated on curing, which leads to blistering and mechanically weak polymers. Moreover, the long-chain aldehydes released, owing to inadequate compatibility with the cured polyurethane, have a tendency to plasticizer migration, which can be manifested by bleeding, substrate discoloration or stress cracking in the substrate. This document likewise discloses oxazolidines derived from lily aldehyde. However, these araliphatic oxazolidines have only very limited storage stability together with isocyanates and cause strong and long-lasting odor immissions as a result of lily aldehyde released, which is also potentially allergenic.

SUMMARY OF THE INVENTION

It is therefore an object of the present invention to provide oxazolidines that are suitable as latent curing agents for polyurethanes and overcome the drawbacks of the prior art.

It has been found that, surprisingly, this object is achieved by a compound of the formula (I) as described in claim 1. The compound of the formula (I) contains at least one optionally substituted oxazolidino group or structurally related groups having a six-membered rather than a five-membered ring structure or having sulfur or tertiary amine in place of the oxygen in the ring. The compound of formula (I) provides oxazolidine curing agents that are liquid throughout the typical use temperature range, do not crystallize even over a prolonged storage period of several months to one year or more and at the same time are of surprisingly low viscosity, are storable together with all kinds of isocyanates and, on hydrolysis, release an odorless, nonvolatile and colorless blocking agent. They can thus be handled in a simple manner and used without restrictions even indoors and in light-colored products. Compositions containing isocyanate groups and comprising such oxazolidine curing agents are notable for good storage stability, even together with very reactive aromatic isocyanates, and cure with moisture rapidly, completely and without blistering, with assurance of an adequate open time, to give high-quality polyurethane polymers. The aldehyde released does not cause any odor immissions here, which means that such polyurethane compositions are also suitable for use indoors and for large-area applications. Curing gives rise to high-quality polymers having high mechanical strength and extensibility, a moderate modulus of elasticity and good heat stability.

Surprisingly, the cured polymers do not show any tendency at all to a tacky surface or substrate damage owing to enhanced plasticizer migration, in spite of the aldehyde of the formula (IV) that has not been incorporated chemically into the polyurethane matrix and is released in the course of curing. This is particularly surprising since this aldehyde has a comparatively high molecular weight and is correspondingly present in the polymer in a comparatively high proportion by weight, and since it bears a long-chain, extremely hydrophobic radical as a substituent, which would suggest poor compatibility if anything with the hydrophilic polymer skeleton of polyurethanes that has hydrogen bonds and hence a strong tendency to plasticizer migration.

Further aspects of the invention are the subject of further independent claims. Particularly preferred embodiments of the invention are the subject of the dependent claims.

WAYS OF EXECUTING THE INVENTION

The invention provides a compound of the formula (I)

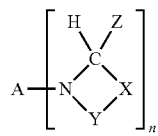

(I)

where
n is 1, 2 or 3,
Z is an aryl radical substituted by an alkyl or alkoxy group and having a total of 12 to 26 carbon atoms,
A is an n-valent organic radical having a molecular weight in the range from 15 to 10 000 g/mol,
X is O or S or $NR^0$ where $R^0$ is a monovalent organic radical having 1 to 18 carbon atoms and
Y is a 1,2-ethylene or 1,3-propylene radical, which is optionally substituted, where A and Y in the case that n=1 may also be bonded to a trivalent radical having 4 to 10 carbon atoms.

A "silane group" refers to a silyl group bonded to an organic radical and having one to three, especially two or three, alkoxy radicals on the silicon atom. "Molecular weight" refers to the molar mass (in g/mol) of a molecule or a molecule residue. "Average molecular weight" refers to the number-average molecular weight ($M_n$) of a polydisperse mixture of oligomeric or polymeric molecules or molecule residues. It is typically determined by means of gel permeation chromatography (GPC) against polystyrene as standard.

A dotted line in the formulae in each case represents the bond between a substituent and the corresponding molecular radical.

A "primary amino group" refers to an amino group which is bonded to a single organic radical and bears two hydrogen atoms; a "secondary amino group" refers to an amino group which is bonded to two organic radicals which may also together be part of a ring and bears one hydrogen atom; and a "tertiary amino group" refers to an amino group which is bonded to three organic radicals, two or three of which may also be part of one or more rings, and does not bear any hydrogen atom.

A "primary diamine" refers to a compound having two primary amino groups.

An "aromatic isocyanate" refers to an isocyanate wherein the isocyanate groups are bonded directly to an aromatic carbon atom. Accordingly, isocyanate groups of this kind are referred to as "aromatic isocyanate groups". An "aliphatic isocyanate" refers to an isocyanate wherein the isocyanate groups are bonded directly to an aliphatic carbon atom. Accordingly, isocyanate groups of this kind are referred to as "aliphatic isocyanate groups". Substance names beginning with "poly", such as polyamine, polyol or polyisocyanate, refer to substances containing, in a formal sense, two or more of the functional groups that occur in their name per molecule.

A substance or composition is referred to as "storage-stable" or "storable" when it can be stored at room temperature in a suitable container over a prolonged period, typically over at least 3 months to up to 6 months or more, without any change in its application or use properties to a degree of relevance for the use thereof as a result of the storage.

"Room temperature" refers to a temperature of 23° C.

"Plasticizers" refer to liquid or dissolved substances which are not chemically incorporated within a cured polymer and typically exert a plasticizing effect on the polymer.

Preferably, n is 1 or 2. These compounds of the formula (I) are particularly easily obtainable and enable particularly storage-stable one-component polyurethane compositions.

Preferably, A is an n-valent aliphatic, cycloaliphatic or arylaliphatic hydrocarbyl radical optionally having oxygen or nitrogen or silicon atoms and having a molecular weight in the range from 15 to 6'000 g/mol.

More preferably, A is an n-valent aliphatic, cycloaliphatic or arylaliphatic hydrocarbyl radical having a molecular weight in the range from 15 to 6'000 g/mol and optionally having one or more groups selected from ether, ester, amino, aldimino, hydroxyl, amido, carbonate, urethane, urea, nitrile and silane groups.

A preferably has a molecular weight in the range from 15 to 2'000 g/mol.

In particular, A is an n-valent aliphatic, cycloaliphatic or arylaliphatic hydrocarbyl radical having a molecular weight in the range from 15 to 2'000 g/mol and optionally having one or more ether, ester, aldimino, hydroxyl, carbonate, urethane or silane groups.

X is preferably O or $NR^0$.

More preferably, X is O.

$R^0$ is preferably an alkyl, cycloalkyl or arylalkyl radical having 1 to 18 carbon atoms and optionally bearing one or two groups selected from carboxylic ester, nitrile, nitro, phosphonic ester, sulfone and sulfonic ester groups.

More preferably, $R^0$ is an alkyl, cycloalkyl or arylalkyl radical having 1 to 12 carbon atoms and optionally bearing one or two carboxylic ester or nitrile groups.

Y is preferably a 1,2-ethylene or 1,3-propylene or 1,2-propylene radical or is an optionally substituted 3-alkyloxy-1,2-propylene or 3-aryloxy-1,2-propylene radical optionally having a silane group, or, in the case that n=1 and X=O, may also be a radical of the formula

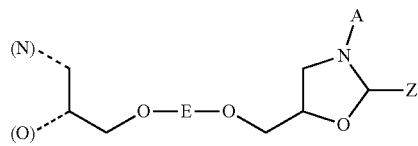

where E is a divalent hydrocarbyl radical which has 6 to 20 carbon atoms and optionally bears one or more ether, ester or glycidoxy groups.

E is preferably the radical of a glycidyl ether after removal of two glycidoxy groups, especially 4,4'-methylenediphenyl, 4,4'-(2,2-propylene)diphenyl, 1,2- or 1,3- or 1,4-phenyl, 1,4-butylene, 1,6-hexylene or α,ω-polyoxypropylene having an average molecular weight in the range from 96 to 1'000 g/mol.

Y is preferably a 1,2-ethylene or 1,2-propylene or 3-alkyloxy-1,2-propylene or 3-aryloxy-1,2-propylene radical, or a 3-alkyloxy-1,2-propylene radical having a silane group.

More preferably, Y is 1,2-ethylene or 3-alkyloxy-1,2-propylene or 3-aryloxy-1,2-propylene.

A compound of formula (I) in which X is O and Y is a radical in which N and O are separated by two carbon atoms is an oxazolidine. An oxazolidine enables compositions having particularly rapid curing when used as a latent curing agent.

A compound of formula (I) in which X is O and Y is a radical in which N and O are separated by three carbon atoms is an oxazinane. An oxazinane enables compositions having particularly good storage stability when used as a latent curing agent.

Z is preferably a radical of the formula (II)

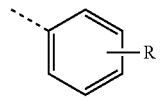

(II)

where R is an alkyl or alkoxy radical having 6 to 20, preferably 8 to 16, carbon atoms.

R is preferably a branched radical. Such a compound of formula (I) is of particularly low viscosity.

R is more preferably a branched alkyl radical having 10 to 14 carbon atoms or a branched alkoxy radical having 8 to 12 carbon atoms.

R is especially a branched alkyl radical having 10 to 14 carbon atoms.

Most preferably, R is a radical of the formula

where $R^1$ and $R^2$ are each an alkyl radical and together have 9 to 13 carbon atoms.

R is preferably in the meta or para position, especially in the para position. Such Z radicals are particularly readily obtainable.

Most preferably, Z is thus a radical of the formula (II a)

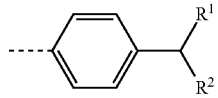

(IIa)

where $R^1$ and $R^2$ have the definitions given.

The preferred Z radicals are particularly readily obtainable and enable compounds of the formula (I) that are typically liquid at room temperature and of particularly low viscosity.

A preferred embodiment of the invention is a compound of the formula (I) in which n is 1, Y is 1,2-ethylene, X is O and A is $A^1$ where $A^1$ is an alkyl, cycloalkyl or aralkyl radical which has 1 to 8 carbon atoms and optionally has a hydroxyl group, especially methyl, ethyl, n-propyl, isopropyl, n-butyl, isobutyl, 2-butyl, tert-butyl, n-hexyl, isohexyl, 2-ethylhexyl or 2-hydroxyethyl.

Such a compound has the formula (I a). It is particularly suitable as a latent curing agent and/or as a drying agent for polyurethane compositions. If the A radical has a hydroxyl group, the compound of the formula (I a) is also suitable as reactant for the preparation of compounds of the formula (I) formed therefrom that have ester, urethane or carbonate groups.

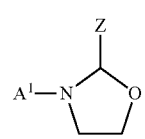

(Ia)

In the formula (I a), $A^1$ and Z have the definitions described.

More preferably, $A^1$ is methyl, ethyl, propyl, isopropyl or n-butyl.

A further preferred embodiment of the invention is a compound of the formula (I) in which n is 1, X is O and A is $A^2$ where $A^2$ is an alkyl radical having a silane group and having 1 to 6 carbon atoms, especially 3-trimethoxysilylpropyl, 3-triethoxysilylpropyl or 3-dimethoxymethylsilylpropyl. Such a compound has the formula (I b). It is particularly suitable as adhesion promoter for polyurethane compositions.

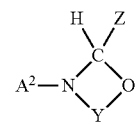

(Ib)

In the formula (I b), $A^2$, Y and Z have the definitions described.

Preferred compounds of the formula (I b) are

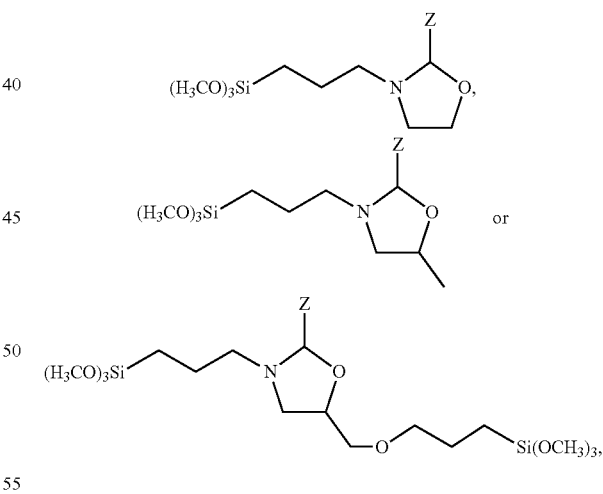

and corresponding compounds having ethoxy groups in place of the methoxy groups on the silicon atom.

A further preferred embodiment of the invention is a compound of the formula (I) in which n is 1, X is O and A is Z—CH=N-$A^3$- where $A^3$ is an alkylene, cycloalkylene or arylalkylene radical having 1 to 8 carbon atoms.

Such a compound has the formula (I c). It is especially an aldimino-oxazolidine and is particularly suitable as a latent curing agent for polyurethane compositions.

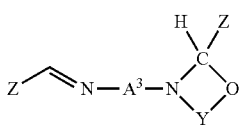

(Ic)

In the formula (I c), $A^3$, Y and Z have the definitions described.

Preferably, Y here is an ethylene or 3-alkyloxy-1,2-propylene or 3-aryloxy-1,2-propylene radical.

Particularly preferred compounds of the formula (I c) are

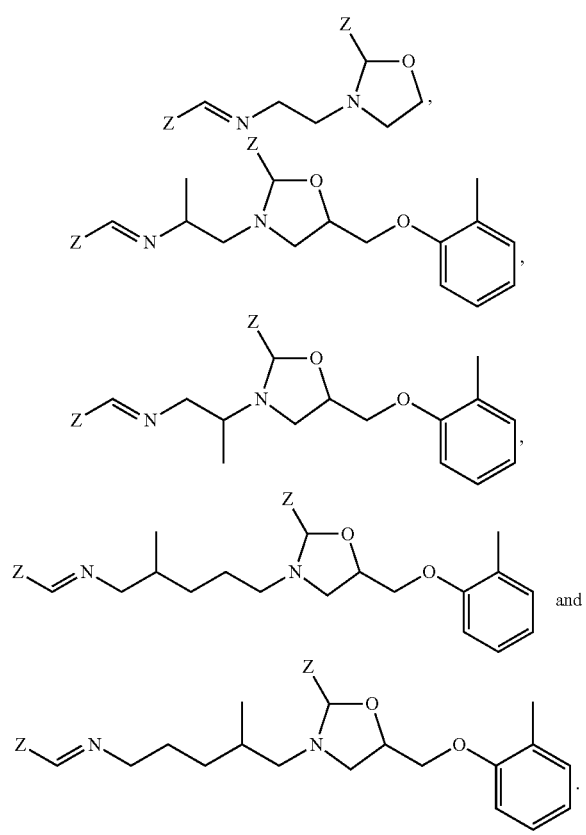

A further preferred embodiment of the invention is a compound of the formula (I) in which n is 2 and A is $A^4$ where $A^4$ is an alkylene or cycloalkylene or arylalkylene radical optionally bearing one or more ether, ester, carbonate or urethane groups and having 2 to 50 carbon atoms.

Such a compound has the formula (I d). Preferably, X in each case is O. It is thus especially a bisoxazolidine and is particularly suitable as a latent curing agent for polyurethane compositions.

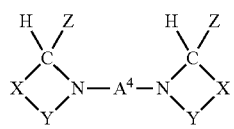

(Id)

In the formula (I d), $A^4$, X, Y and Z have the definitions already described.

Preferably, X is O.

Preferably, Y is 1,2-ethylene, 1,2-propylene or 1,3-propylene, especially 1,2-ethylene.

Preferably, $A^4$ is an alkylene or cycloalkylene or arylalkylene radical bearing two urethane groups and having 10 to 20 carbon atoms.

Further preferably, $A^4$ is an alkylene radical bearing a carbonate group and having 5 to 7 carbon atoms.

Further preferably, $A^4$ is an alkylene or cycloalkylene or arylalkylene radical optionally bearing one or more ether groups and having 2 to 15 carbon atoms.

Further preferably, $A^4$ is an alkylene or cycloalkylene or arylalkylene radical bearing two ester groups and having 10 to 20 carbon atoms.

Particularly preferred compounds of the formula (I d) are

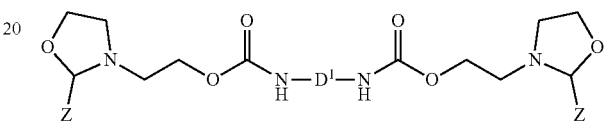

where $D^1$ is a divalent hydrocarbyl radical having 6 to 15 carbon atoms, especially 1,6-hexylene or (1,5,5-trimethylcyclohexan-1-yl)methane-1,3 or 4(2)-methyl-1,3-phenylene,

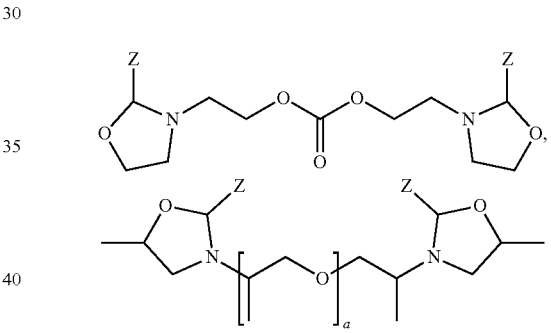

with a=2 or 3,

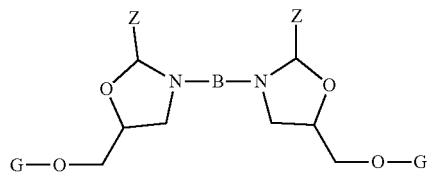

where B is an alkylene or cycloalkylene or arylalkylene radical which optionally has ether oxygen and has 2 to 15 carbon atoms and G is a hydrocarbyl radical which optionally has ether oxygen and has 2 to 25 carbon atoms, especially phenyl, a substituted phenyl or 2-ethylhexyl,

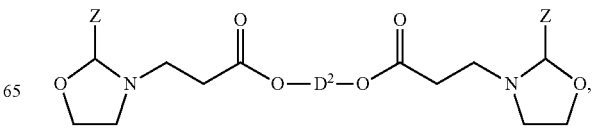

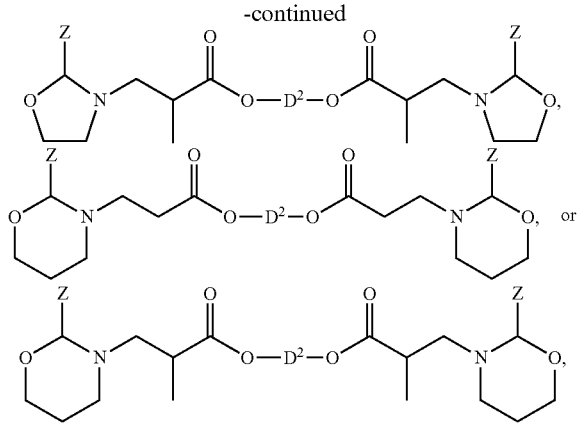

where $D^2$ is an alkylene or cycloalkylene or arylalkylene radical optionally having ether oxygen and having 2 to 15 carbon atoms.

Most preferred compounds of the formula (I d) are the diurethanes of the formula

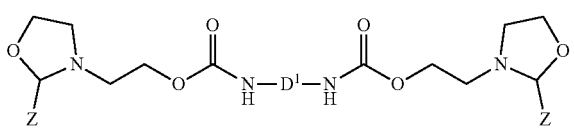

A further preferred embodiment of the invention is a compound of the formula (I) in which n is 1, X is O, A is $A^5$ and Y is a radical of the formula

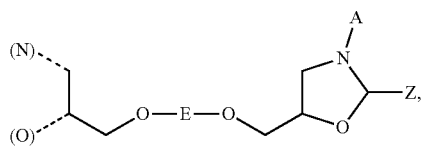

where $A^5$ is an alkyl, cycloalkyl or aralkyl radical optionally bearing one or more ether groups and having 1 to 35 carbon atoms, especially methyl, ethyl, n-propyl, isopropyl, n-butyl, isobutyl, 2-butyl, tert-butyl, n-hexyl, isohexyl, 2-ethylhexyl, dodecyl or a methoxy-terminated polyoxypropylene radical that may also contain oxyethylene components.

Such a compound has the formula (I e). It is a bisoxazolidine and is particularly suitable as a latent curing agent for polyurethane compositions.

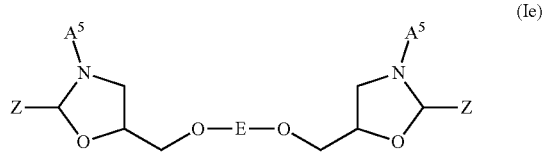

In the formula (I e), $A^5$, E and Z have the definitions already described.

A further preferred embodiment of the invention is a compound of the formula (I) in which n is 1, A and Y are joined to form a trivalent aliphatic hydrocarbon radical having an additional X and an additional Z and having 4 to 10 carbon atoms, and X is O.

Such a compound especially has the formula (I f)

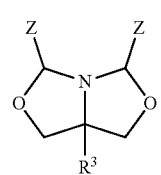

where $R^3$ is an alkyl radical having 1 to 4 carbon atoms, especially methyl or ethyl, and Z has the definitions already given.

It is a fused bisoxazolidine and is particularly suitable as a latent curing agent for polyurethane compositions.

The compound of the formula (I) is preferably obtained from the reaction of at least one amine of the formula (III) with at least one aldehyde of the formula (IV) in a condensation reaction with removal of water.

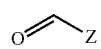

where A, X, n and Z have the definitions already given.

If A in formula (I) has an aldimino group, there is especially a primary amino group at the corresponding site for A in formula (III).

The aldehyde of the formula (IV) is here used stoichiometrically or especially in a stoichiometric excess with respect to the XH groups.

The reaction is preferably conducted in such a way that
the amine of the formula (III) is combined with the aldehyde of the formula (IV) to give a reaction mixture, the aldehyde being used stoichiometrically or especially in a stoichiometric excess with respect to the XH groups,
and the water of condensation and any solvent present are removed from the reaction mixture by a suitable method during or after the combining, optionally with heating thereof and/or application of reduced pressure.

The water of condensation is preferably removed from the heated reaction mixture by means of application of reduced pressure without using solvents.

A compound of the formula (I) in which A has one or more ester, carbonate or urethane groups can especially also be obtained by reacting a compound of the formula (I) having a hydroxyl group with a mono- or polyfunctional carboxylic ester or carbonate or isocyanate.

The compound of the formula (I) having hydroxyl groups which is used here is especially a compound of the formula (I a) in which $A^1$ has a hydroxyl group. Most preferably, a compound of the formula

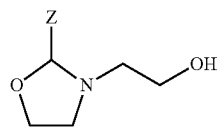

in which Z has the definitions already described is used here.

Particular preference is given to reaction with a carbonate or a commercially available monomeric diisocyanate such as, in particular, hexamethylene 1,6-diisocyanate (HDI), 1-isocyanato-3,3,5-trimethyl-5-isocyanatomethylcyclohexane (IPDI) or tolylene 2,4- or 2,6-diisocyanate or any mixtures of these isomers (TDI).

A compound of the formula (I) in which A has one or more ester, amido or nitrile groups is also obtainable in that a compound of the formula

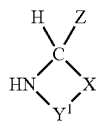

in which $Y^1$ is a 1,2-ethylene or 1,3-propylene or 1,2-propylene radical and X and Z have the definitions already given is reacted with a Michael acceptor, especially a (meth)acrylic ester, maleic ester or fumaric ester, citraconic ester or itaconic ester, or an amide of these esters, or acrylonitrile.

The compound of the formula

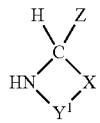

is itself obtainable from the reaction of an amine of the formula $H_2N$—$Y^1$—XH with the aldehyde of the formula (IV).

Some suitable amines of the formula (III) for the reaction with the aldehyde of the formula (IV) for preparation of a compound of the formula (I) are commercially available, or they can be prepared in a simple manner from commercially available starting materials.

A suitable amine of the formula (III) is a commercially available aliphatic hydroxylamine such as, in particular, N-methylethanolamine, N-ethylethanolamine, N-n-propylethanolamine, N-isopropylethanolamine, N-n-butylethanolamine, N-isobutylethanolamine, N-2-butylethanolamine, N-tert-butylethanolamine, N-n-hexylethanolamine, N-isohexylethanolamine or N-(2-ethylhexyl)ethanolamine.

Such an amine of the formula (III) is particularly suitable for the preparation of a compound of the formula (I a) which is free of hydroxyl groups.

A further suitable amine of the formula (III) is a commercially available aliphatic dihydroxylamine such as, in particular, diethanolamine or diisopropanolamine. Such an amine of the formula (III) is particularly suitable for the preparation of compounds of the formula (I a) having a hydroxyl group, which is then preferably reacted with a carbonate or diisocyanate or ester to give a compound of the formula (I d).

A further suitable amine of the formula (III) is an aminosilane, such as, in particular, 3-aminopropyltrimethoxysilane, 3-aminopropyltriethoxysilane or 3-aminopropyldimethoxymethylsilane, that has been reacted with an epoxide such as, in particular, ethylene oxide, propylene oxide, 3-glycidoxypropyltrimethoxysilane, 3-glycidoxypropyltriethoxysilane, phenyl glycidyl ether, cresyl glycidyl ether or an alkyl glycidyl ether. It has to be ensured here that the hydroxyl group formed in the reaction with the epoxide reacts to a minimum degree with the silane group. A speedy further reaction with the aldehyde of the formula (IV) is thus advantageous. In the reaction with the aldehyde, it also has to be ensured that the silane group is hydrolyzed to a minimum degree with the water released. Preference is given to rapid removal of the water and optionally additional use of desiccants, for example molecular sieve.

Such an amine of the formula (III) is particularly suitable for the preparation of a compound of the formula (I b).

A further suitable amine of the formula (III) is an amine of the formula (III) in which n is 1 and A has a primary amino group, such as, in particular, N-(2-aminoethyl)ethanolamine or reaction products of primary diamines with monoepoxides in a molar ratio of 1:1. Particular preference is given to the reaction product of a superstoichiometric amount of propane-1,2-diamine or 2-methylpentane-1,5-diamine with cresyl glycidyl ether and subsequent removal of unconverted propane-1,2-diamine or 2-methylpentane-1,5-diamine.

Such an amine of formula (III) is particularly suitable for the preparation of a compound of formula (I c) which is an aldimino-oxazolidine.

A further suitable amine of the formula (III) is a difunctional compound that has a 2-hydroxyethylamino or 2-hydroxypropylamino group at either terminal end. Such an amine is especially obtainable by reacting a commercially available primary amine with 2 mol of ethylene oxide or propylene oxide.

Such an amine is also obtainable by the reaction of a commercially available primary amine with 2 mol of a commercially available monoglycidyl ether such as, in particular, phenyl glycidyl ether, cresyl glycidyl ether, tert-butylphenyl glycidyl ether, cardanol glycidyl ether or 2-ethylhexyl glycidyl ether.

Such an amine is also obtainable by the reaction of 2 mol of ethanolamine or isopropanolamine or 3-amino-1-propanal with a commercially available diacrylate or dimethacrylate such as, in particular, butanediol diacrylate, hexanediol diacrylate, methylpentanediol diacrylate, butanediol dimethacrylate or hexanediol dimethacrylate.

These amines of the formula (III) are particularly suitable for the preparation of a compound of the formula (I d).

Likewise possible is the reaction of a polyfunctional acrylate such as, in particular, trimethylolpropane triacrylate with ethanolamine or isopropanolamine or 3-amino-1-propanol, giving compounds of the formula (I) with n=3.

A further suitable amine of the formula (III) is a reaction product from the reaction of a monoamine, such as, in particular, methylamine, ethylamine, n-propylamine, isopropylamine, n-butylamine, isobutylamine, 2-butylamine, tert-butylamine, n-hexylamine, isohexylamine, 2-ethylhexylamine, dodecylamine, benzylamine or a methoxy-terminated polyoxyalkyleneamine such as, in particular, Jeffamine® M-600 (from Huntsman), with a diepoxide, especially a commercially available diglycidyl ether such as, in particular, butanediol diglycidyl ether, hexanediol diglycidyl ether, dipropylene glycol diglycidyl ether, polypropylene glycol diglycidyl ether, bisphenol A diglycidyl ether or bisphenol F diglycidyl ether.

Such an amine of the formula (III) is particularly suitable for the preparation of a compound of the formula (I e).

A suitable amine of the formula (III) is also a primary amine having two hydroxyl groups, such as, in particular, 2-amino-2-ethylpropane-1,3-diol. This amine is especially suitable for the preparation of a compound of the formula (I f), which is a fused bisoxazolidine.

Suitable commercially available primary diamines are especially hexane-1,6-diamine, 2-methylpentane-1,5-diamine, 2,2(4),4-trimethylhexamethylenediamine, 1-amino-3-aminomethyl-3,5,5-trimethylcyclohexane, 4(2)-methylcyclohexane-1,3-diamine, cyclohexane-1,2-diamine, bis(4-aminocyclohexyl)methane, 1,3-bis(aminomethyl)cyclohexane, 1,4-bis(aminomethyl)cyclohexane, 1,3-bis(aminomethyl)benzene, polyoxypropylenediamine having an average molecular weight in the range from 200 to 2'000 g/mol, especially from 200 to 500 g/mol, or trimethylolpropane- or glycerol-started polyoxypropylenetriamine having an average molecular weight in the range from 380 to 500 g/mol.

A preferred aldehyde of the formula (IV) is an aldehyde of the formula (IV a) where R has the definitions already described.

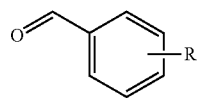

(IVa)

A particularly preferred aldehyde of the formula (IV) is an aldehyde of the formula (IV b) where $R^1$ and $R^2$ have the definitions already described.

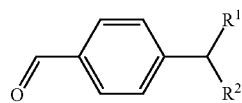

(IVb)

Preferred aldehydes of the formula (IV) are benzaldehydes that bear, in the 3 or 4 position, especially in the 4 position, a branched alkyl or alkoxy radical having 6 to 20, especially 8 to 16, carbon atoms, especially 4-octylbenzaldehyde, 4-nonylbenzaldehyde, 4-decylbenzaldehyde, 4-undecylbenzaldehyde, 4-dodecylbenzaldehyde, 4-tridecylbenzaldehyde, 4-tetradecylbenzaldehyde, 4-pentadecylbenzaldehyde, 4-hexadecylbenzaldehyde, 4-hexyloxybenzaldehyde, 4-heptyloxybenzaldehyde, 4-octyloxybenzaldehyde, 4-nonyloxybenzaldehyde, 4-decyloxybenzaldehyde, 4-undecyloxybenzaldehyde, 4-dodecyloxybenzaldehyde, 4-tridecyloxybenzaldehyde or 4-tetradecyloxybenzaldehyde, where the 4-alkyl and alkoxy radicals are each branched.

Particularly preferred aldehydes of the formula (IV) are benzaldehydes that bear a branched $C_{10-14}$-alkyl radical in the 3 or 4 position, especially in the 4 position, especially 4-decylbenzaldehyde, 4-undecylbenzaldehyde, 4-dodecylbenzaldehyde, 4-tridecylbenzaldehyde or 4-tetradecylbenzaldehyde.

Most preferred as aldehyde of the formula (IV) is a mixture comprising 4-decylbenzaldehydes, 4-undecylbenzaldehydes, 4-dodecylbenzaldehydes, 4-tridecylbenzaldehydes or 4-tetradecylbenzaldehydes, the alkyl radicals of which are mainly branched.

The aldehyde of the formula (IV) is especially obtainable from the formylation of at least one alkyl- and/or alkoxy-substituted aromatic hydrocarbon with carbon monoxide under the action of an acid catalyst. An example of a suitable acid catalyst is the HCl—AlCl$_3$ system (Gattermann-Koch reaction).

In a preferred preparation process, the formylation is conducted with HF—BF$_3$ as acid catalyst. This is advantageous since this process proceeds particularly selectively and the aldehyde of the formula (IV) can be separated from the reaction mixture without a hydrolysis step and the catalyst can be reused, which means that costly and inconvenient product workup and disposal of waste is dispensed with.

Preferably, the compound of the formula (I) is a mixture of compounds of the formula (I) in which each Z is a radical of the formula (II) and R is selected from alkyl radicals having 6 to 20 carbon atoms that are mainly branched. R is more preferably selected from mainly branched decyl, undecyl, dodecyl, tridecyl and tetradecyl radicals.

The invention thus further provides a mixture of compounds of the formula (I) in which each Z is a radical of the formula (II) and R is selected from mainly branched 4-decyl, 4-undecyl, 4-dodecyl, 4-tridecyl and 4-tetradecyl radicals.

A mixture of this kind is particularly easily industrially obtainable.

It is a feature of the compound of the formula (I) that it is nonvolatile and entirely odorless as such and also in hydrolyzed form, and hence does not lead to any immissions at all and can be used without nuisance to the processor and user even indoors and for large-area applications without any need for protective measures. Furthermore, the compound of the formula (I) is colorless and can thus also be used in light-colored products. Finally, it is typically liquid both at room temperature and at winter temperatures and can thus be processed easily and without use of solvents even in the case of unheated storage and transport.

The invention further provides for the use of at least one compound of the formula (I) as latent curing agent for compositions containing isocyanate groups.

The compound of the formula (I) has advantageous properties for the use described. It has excellent miscibility into compositions containing isocyanate groups and shows barely any tendency to separation. It triggers barely any crosslinking reactions of the isocyanate groups in the absence of water or moisture and thus enables good storage stability. On ingress of moisture, it reacts rapidly with isocyanate groups present under hydrolysis, which proceeds largely without competing isocyanate hydrolysis and hence without blistering. And finally, the aldehyde released in the curing is nonvolatile and hydrolysis-stable, does not cause any odor nuisance and surprisingly has excellent compatibility with the cured polymer, barely bleeds out and barely migrates into the substrates.

In one embodiment of the invention, the compound of the formula (I) is used as desiccant for compositions that cure with moisture, especially compositions containing isocyanate groups. For this purpose, the compound of the formula (I) is additionally used in the production of the composition and reacts with moisture present in the course of production. Suitable compounds for use as desiccants are especially compounds of the formula (I a), especially those in which the $A^1$ radical is free of hydroxyl groups.

In a further embodiment of the invention, the compound of the formula (I) is used as adhesion promoter for compositions that cure with moisture, especially compositions containing isocyanate groups. Especially suitable compounds for this use are those of the formula (I b) that have at least one silane group. Particularly suitable compounds of the formula (I b) are those in which the Y radical has a further silane group. Such compounds of the formula (I b) are especially obtained from the reaction of aminosilanes with epoxysilanes and aldehydes of the formula (IV).

The invention further provides a composition comprising
at least one compound of formula (I) and
at least one polyisocyanate and/or at least one polyurethane polymer containing isocyanate groups.

Suitable compounds of the formula (I) are those described above. Particularly suitable compounds are those of the formula (I c), (I d), (I e) or (I f). Most suitable are compounds of the formula (I c) or (I d).

A suitable polyisocyanate is especially a commercially available polyisocyanate, especially aromatic di- or triisocyanates, preferably diphenylmethane 4,4'- or 2,4'- or 2,2'-diisocyanate or any mixtures of these isomers (MDI), tolylene 2,4- or 2,6-diisocyanate or any mixtures of these isomers (TDI), mixtures of MDI and MDI homologs (polymeric MDI or PMDI), phenylene 1,3- or 1,4-diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), tris(4-isocyanatophenyl)methane or tris(4-isocyanatophenyl) thiophosphate; preferably MDI or TDI;

aliphatic, cycloaliphatic or arylaliphatic di- or triisocyanates, preferably tetramethylene 1,4-diisocyanate, 2-methylpentamethylene 1,5-diisocyanate, hexamethylene 1,6-diisocyanate (HDI), 2,2,4- and/or 2,4,4-trimethylhexamethylene 1,6-diisocyanate (TMDI), decamethylene 1,10-diisocyanate, dodecamethylene 1,12-diisocyanate, lysine diisocyanate or lysine ester diisocyanate, cyclohexane 1,3- or 1,4-diisocyanate, 1-methyl-2,4- and/or -2,6-diisocyanatocyclohexane ($H_6$TDI), 1-isocyanato-3,3,5-trimethyl-5-isocyanatomethylcyclohexane (IPDI), perhydrodiphenylmethane 2,4'- and/or 4,4'-diisocyanate ($H_{12}$MDI), 1,3- or 1,4-bis(isocyanatomethyl)cyclohexane, m- or p-xylylene diisocyanate, tetramethylxylylene 1,3- or 1,4-diisocyanate, 1,3,5-tris(isocyanatomethyl)benzene, bis(1-isocyanato-1-methylethyl)naphthalene, dimer or trimer fatty acid isocyanates, such as, especially, 3,6-bis(9-isocyanatononyl)-4,5-di(1-heptenyl)cyclohexene (dimeryl diisocyanate); preferably $H_{12}$MDI or HDI or IPDI;

oligomers or derivatives of the di- or triisocyanates mentioned, especially derived from HDI, IPDI, MDI or TDI, especially oligomers containing uretdione or isocyanurate or iminooxadiazinedione groups or various groups among these; or di- or polyfunctional derivatives containing ester or urea or urethane or biuret or allophanate or carbodiimide or uretonimine or oxadiazinetrione groups or various groups among these. In practice, polyisocyanates of this kind are typically mixtures of substances having different degrees of oligomerization and/or chemical structures. They especially have an average NCO functionality of 2.1 to 4.0.

Preferred polyisocyanates are aliphatic, cycloaliphatic or aromatic diisocyanates, especially HDI, TMDI, cyclohexane 1,3- or 1,4-diisocyanate, IPDI, $H_{12}$MDI, 1,3- or 1,4-bis(isocyanatomethyl)cyclohexane, XDI, TDI, MDI, phenylene 1,3- or 1,4-diisocyanate or naphthalene 1,5-diisocyanate (NDI).

A particularly preferred polyisocyanate is HDI, IPDI, $H_{12}$MDI, TDI, MDI or a form of MDI which is liquid at room temperature, especially HDI, IPDI, TDI or MDI.

A form of MDI which is liquid at room temperature is either 4,4'-MDI liquefied by partial chemical modification—especially carbodiimidization or uretonimine formation or adduct formation with polyols—or it is a mixture of 4,4'-MDI with other MDI isomers (2,4'-MDI and/or 2,2'-MDI), and/or with MDI oligomers and/or MDI homologs (PMDI), that has been brought about selectively by blending or results from the production process.

Most preferred is IPDI, TDI or MDI.

A suitable polyurethane polymer containing isocyanate groups is especially obtained from the reaction of at least one polyol with a superstoichiometric amount of at least one polyisocyanate. The reaction is preferably conducted with exclusion of moisture at a temperature in the range from 50 to 160° C., optionally in the presence of suitable catalysts. The NCO/OH ratio is preferably in the range from 1.3/1 to 5/1, preferably 1.5/1 to 4/1, especially 1.8/1 to 3/1. The polyisocyanate remaining in the reaction mixture after the conversion of the OH groups, especially monomeric diisocyanate, can be removed, especially by means of distillation, which is preferable in the case of a high NCO/OH ratio. The polyurethane polymer obtained preferably has a content of free isocyanate groups in the range from 1% to 10% by weight, especially 1.5% to 6% by weight. The polyurethane polymer can optionally be prepared with additional use of plasticizers or solvents, in which case the plasticizers or solvents used do not contain any groups reactive toward isocyanates.

Preferred polyisocyanates for preparation of a polyurethane polymer containing isocyanate groups are the polyisocyanates already mentioned, especially the diisocyanates, preferably MDI, TDI, IPDI, HDI or $H_{12}$MDI, especially MDI, TDI, IPDI or HDI.

Suitable polyols are commercial polyols or mixtures thereof, especially polyether polyols, especially polyoxyalkylenediols and/or polyoxyalkylenetriols, especially polymerization products of ethylene oxide or 1,2-propylene oxide or 1,2- or 2,3-butylene oxide or oxetane or tetrahydrofuran or mixtures thereof, where these may be polymerized with the aid of a starter molecule having two or more active hydrogen atoms, especially a starter molecule such as water, ammonia or a compound having multiple OH or NH groups, such as, for example, ethane-1,2-diol, propane-1,2- or -1,3-diol, neopentyl glycol, diethylene glycol, triethylene glycol, the isomeric dipropylene glycols or tripropylene glycols, the isomeric butanediols, pentanediols, hexanediols, heptanediols, octanediols, nonanediols, decanediols, undecanediols, cyclohexane-1,3- or -1,4-dimethanol, bisphenol A, hydrogenated bisphenol A, 1,1,1-trimethylolethane, 1,1,1-trimethylolpropane, glycerol or aniline, or mixtures of the abovementioned compounds. Likewise suitable are polyether polyols with polymer particles dispersed therein, especially those with styrene/acrylonitrile (SAN) particles or polyurea or polyhydrazodicarbonamide (PHD) particles.

Preferred polyether polyols are polyoxypropylene diols or polyoxypropylene triols, or what are called ethylene oxide-terminated (EO-endcapped) polyoxypropylene diols or triols. The latter are mixed polyoxyethylene/polyoxypropylene polyols which are especially obtained in that polyoxypropylene diols or triols, on conclusion of the polypropoxylation reaction, are further alkoxylated with ethylene oxide and thereby eventually have primary hydroxyl groups.

Preferred polyether polyols have a degree of unsaturation of less than 0.02 meq/g, especially less than 0.01 meq/g.

Polyester polyols, also called oligoesterols, prepared by known processes, especially the polycondensation of hydroxycarboxylic acids or lactones or the polycondensation of aliphatic and/or aromatic polycarboxylic acids with di- or polyhydric alcohols. Preference is given to polyester diols from the reaction of dihydric alcohols, such as, especially, 1,2-ethanediol, diethylene glycol, 1,2-propanediol, dipropylene glycol, 1,4-butanediol, 1,5-pentanediol, 1,6-hexanediol, neopentyl glycol, glycerol, 1,1,1-trimethylolpropane or mixtures of the abovementioned alcohols, with organic dicarboxylic acids or the anhydrides or esters thereof, such as, especially, succinic acid, glutaric acid, adipic acid, suberic acid, sebacic acid, dodecanedicarboxylic acid, maleic acid, fumaric acid, phthalic acid, isophthalic acid, terephthalic acid or hexahydrophthalic acid or mixtures of the abovementioned acids, or polyester polyols from lactones, such as, especially, ε-caprolactone. Particular preference is given to polyester polyols from adipic acid or sebacic acid or dodecanedicarboxylic acid and hexanediol or neopentyl glycol.

Polycarbonate polyols as obtainable by reaction, for example, of the abovementioned alcohols—used to form the polyester polyols—with dialkyl carbonates, diaryl carbonates or phosgene.

Block copolymers bearing at least two hydroxyl groups and having at least two different blocks having polyether, polyester and/or polycarbonate structure of the type described above, especially polyether polyester polyols.

Polyacrylate polyols and polymethacrylate polyols.

Polyhydroxy-functional fats and oils, for example natural fats and oils, especially castor oil; or polyols obtained by chemical modification of natural fats and oils—called oleochemical polyols—for example the epoxy polyesters or epoxy polyethers obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes, such as alcoholysis or ozonolysis, and subsequent chemical linkage, for example by transesterification or dimerization, of the degradation products or derivatives thereof thus obtained. Suitable degradation products of natural fats and oils are especially fatty acids and fatty alcohols and also fatty acid esters, especially the methyl esters (FAME), which can be derivatized to hydroxy fatty acid esters by hydroformylation and hydrogenation, for example.

Polyhydrocarbon polyols, also called oligohydrocarbonols, such as, for example, polyhydroxy-functional polyolefins, polyisobutylenes, polyisoprenes; polyhydroxy-functional ethylene/propylene, ethylene/butylene or ethylene/propylene/diene copolymers, as produced, for example, by Kraton Polymers; polyhydroxy-functional polymers of dienes, especially of 1,3-butadiene, which can especially also be prepared from anionic polymerization; polyhydroxy-functional copolymers of dienes, such as 1,3-butadiene, or diene mixtures and vinyl monomers, such as styrene, acrylonitrile, vinyl chloride, vinyl acetate, vinyl alcohol, isobutylene and isoprene, for example polyhydroxy-functional acrylonitrile/butadiene copolymers, as can be prepared, for example, from epoxides or aminoalcohols and carboxyl-terminated acrylonitrile/butadiene copolymers (commercially available, for example, under the Hypro® CTBN or CTBNX or ETBN name from Emerald Performance Materials); and hydrogenated polyhydroxy-functional polymers or copolymers of dienes.

Also especially suitable are mixtures of polyols.

Preference is given to polyether polyols, polyester polyols, polycarbonate polyols, poly(meth)acrylate polyols or polybutadiene polyols.

Particular preference is given to polyether polyols, polyester polyols, especially aliphatic polyester polyols, or polycarbonate polyols, especially aliphatic polycarbonate polyols.

The most preferred are polyether polyols, especially polyoxypropylene di- or triols or ethylene oxide-terminated polyoxypropylene di- or triols.

Preference is given to polyols having an average molecular weight in the range from 400 to 20 000 g/mol, preferably from 1000 to 10 000 g/mol.

Preference is given to polyols having an average OH functionality in the range from 1.6 to 3.

Preference is given to polyols that are liquid at room temperature.

Preference is given to polyols which are solid at room temperature for the preparation of a polyurethane polymer which is solid at room temperature.

In the preparation of a polyurethane polymer containing isocyanate groups, it is also possible to use fractions of di- or polyfunctional alcohols, especially 1,2-ethanediol, 1,2-propanediol, 1,3-propanediol, 2-methyl-1,3-propanediol, 1,2-butanediol, 1,3-butanediol, 1,4-butanediol, 1,3-pentanediol, 1,5-pentanediol, 3-methyl-1,5-pentanediol, neopentyl glycol, dibromoneopentyl glycol, 1,2-hexanediol, 1,6-hexanediol, 1,7-heptanediol, 1,2-octanediol, 1,8-octanediol, 2-ethyl-1,3-hexanediol, diethylene glycol, triethylene glycol, dipropylene glycol, tripropylene glycol, 1,3- or 1,4-cyclohexanedimethanol, ethoxylated bisphenol A, propoxylated bisphenol A, cyclohexanediol, hydrogenated bisphenol A, dimer fatty acid alcohols, 1,1,1-trimethylolethane, 1,1,1-trimethylolpropane, glycerol, pentaerythritol, sugar alcohols, such as especially xylitol, sorbitol or mannitol, or sugars, such as especially sucrose, or alkoxylated derivatives of the alcohols mentioned or mixtures of the alcohols mentioned.

Preference is given to the additional use of butane-1,4-diol for applications in which particularly high strengths are desired.

The polyurethane polymer containing isocyanate groups preferably has an average molecular weight in the range from 1'000 to 20'000 g/mol, especially 1'500 to 10'000 g/mol.

It is preferably liquid at room temperature.

For use in a hotmelt adhesive, preference is given to a polyurethane polymer which is solid at room temperature and has been prepared proceeding from at least one polyol which is solid at room temperature. A suitable polyol which is solid at room temperature is crystalline, partially crystalline or amorphous at room temperature. Its melting point is preferably in the range from 50 to 180° C., especially 70 to 150° C. Preference is given to polyester polyols, especially those derived from hexanediol and adipic acid or dodecanedicarboxylic acid, or acrylate polyols. The polyurethane polymer is especially prepared at a temperature above the melting point of the polymer which is solid at room temperature.

The composition preferably comprises at least one polyurethane polymer containing isocyanate groups.

In addition to a polyurethane polymer comprising isocyanate groups, the composition can furthermore contain at least one diisocyanate and/or one oligomer or polymer of a diisocyanate, especially an IPDI isocyanurate or a TDI oligomer or a mixed isocyanurate based on TDI/HDI or an HDI oligomer or a form of MDI which is liquid at room temperature.

Preferably, the composition comprises, as well as at least one compound of the formula (I) and at least one polyisocyanate and/or polyurethane polymer containing isocyanate groups, additionally one or more further constituents that are especially selected from catalysts, fillers, plasticizers and solvents.

Suitable catalysts are especially catalysts for the hydrolysis of oxazolidino groups, especially organic acids, especially carboxylic acids, such as 2-ethylhexanoic acid, lauric acid, stearic acid, isostearic acid, oleic acid, neodecanoic acid, benzoic acid, salicylic acid or 2-nitrobenzoic acid, organic carboxylic acid anhydrides, such as phthalic anhydride, hexahydrophthalic anhydride or methylhexahydrophthalic anhydride, silyl esters of carboxylic acids, organic sulfonic acids, such as methanesulfonic acid, p-toluenesulfonic acid or 4-dodecylbenzenesulfonic acid, sulfonic acid esters, other organic or inorganic acids, or mixtures of the abovementioned acids and acid esters. Particular preference is given to carboxylic acids, especially aromatic carboxylic acids, such as benzoic acid, 2-nitrobenzoic acid or especially salicylic acid.

Suitable catalysts are furthermore catalysts for the acceleration of the reaction of isocyanate groups, especially organotin(IV) compounds, such as especially dibutyltin diacetate, dibutyltin dilaurate, dibutyltin dichloride, dibutyltin diacetylacetonate, dimethyltin dilaurate, dioctyltin diacetate, dioctyltin dilaurate or dioctyltin diacetylacetonate, complexes of bismuth(III) or zirconium(IV), especially with ligands selected from alkoxides, carboxylates, 1,3-diketonates, oxinate, 1,3-ketoesterates and 1,3-ketoamidates, or compounds containing tertiary amino groups, such as especially 2,2'-dimorpholinodiethyl ether (DMDEE).

Also especially suitable are combinations of different catalysts.

Suitable fillers are especially ground or precipitated calcium carbonates, optionally coated with fatty acids, especially stearates, barytes, quartz flours, quartz sands, dolomites, wollastonites, kaolins, calcined kaolins, sheet silicates, such as mica or talc, zeolites, aluminum hydroxides, magnesium hydroxides, silicas, including finely divided silicas from pyrolysis processes, cements, gypsums, fly ashes, industrially produced carbon blacks, graphite, metal powders, for example of aluminum, copper, iron, silver or steel, PVC powders or hollow beads.

Suitable plasticizers are especially carboxylic acid esters, such as phthalates, especially diisononyl phthalate (DINP), diisodecyl phthalate (DIDP) or di(2-propylheptyl) phthalate (DPHP), hydrogenated phthalates, especially hydrogenated diisononyl phthalate or diisononyl cyclohexane-1,2-dicarboxylate (DINCH), terephthalates, especially dioctyl terephthalate, trimellitates, adipates, especially dioctyl adipate, azelates, sebacates, benzoates, glycol ethers, glycol esters, organic phosphoric or sulfonic acid esters, polybutenes, polyisobutenes or plasticizers derived from natural fats or oils, especially epoxidized soybean or linseed oil.

Suitable solvents are especially acetone, methyl ethyl ketone, methyl n-propyl ketone, diisobutyl ketone, methyl isobutyl ketone, methyl n-amyl ketone, methyl isoamyl ketone, acetylacetone, mesityl oxide, cyclohexanone, methylcyclohexanone, ethyl acetate, propyl acetate, butyl acetate, n-butyl propionate, diethyl malonate, 1-methoxy-2-propyl acetate, ethyl 3-ethoxypropionate, diisopropyl ether, diethyl ether, dibutyl ether, diethylene glycol diethyl ether, ethylene glycol diethyl ether, ethylene glycol monopropyl ether, ethylene glycol mono(2-ethylhexyl) ether, acetals such as, in particular, methylal, ethylal, propylal, butylal, 2-ethylhexylal, dioxolane, glycerol formal or 2,5,7,10-tetraoxaundecane (TOU), and toluene, xylene, heptane, octane, naphtha, white spirit, petroleum ether or petroleum spirit, especially Solvesso™ products (from Exxon), and furthermore methylene chloride, propylene carbonate, butyrolactone, N-methylpyrrolidone or N-ethylpyrrolidone.

The composition may comprise further additives commonly used for polyurethane compositions. More particularly, the following auxiliaries and additives may be present:
- inorganic or organic pigments, especially titanium dioxide, chromium oxides or iron oxides;
- fibers, especially glass fibers, carbon fibers, metal fibers, ceramic fibers, polymer fibers, such as polyamide fibers or polyethylene fibers, or natural fibers, such as wool, cellulose, hemp or sisal;
- dyes;
- desiccants, especially molecular sieve powder, calcium oxide, highly reactive isocyanates, such as p-tosyl isocyanate, monomeric diisocyanates or orthoformic esters;
- adhesion promoters, especially organoalkoxysilanes, especially epoxysilanes, such as especially 3-glycidoxypropyltrimethoxysilane or 3-glycidoxypropyltriethoxysilane, (meth)acrylosilanes, anhydridosilanes, carbamatosilanes, alkylsilanes or iminosilanes, or oligomeric forms of these silanes, or titanates;
- latent curing agents or crosslinkers, especially aldimines, ketimines, enamines or oxazolidines not conforming to the formula (I);
- further catalysts which accelerate the reaction of the isocyanate groups, especially salts, soaps or complexes of tin, zinc, bismuth, iron, aluminum, molybdenum, dioxomolybdenum, titanium, zirconium or potassium, especially tin(II) 2-ethylhexanoate, tin(II) neodecanoate, zinc(II) acetate, zinc(II) 2-ethylhexanoate, zinc(II) laurate, zinc(II) acetylacetonate, aluminum lactate, aluminum oleate, diisopropoxytitanium bis(ethyl acetoacetate) or potassium acetate; compounds containing tertiary amino groups, especially N-ethyldiisopropylamine, N,N,N',N'-tetramethylalkylenediamines, pentamethylalkylenetriamines and higher homologs thereof, bis(N,N-diethylaminoethyl) adipate, tris(3-dimethylaminopropyl)amine, 1,4-diazabicyclo[2.2.2]octane (DABCO), 1,8-diazabicyclo[5.4.0]undec-7-ene (DBU), 1,5-diazabicyclo[4.3.0]non-5-ene (DBN), N-alkylmorpholines, N,N'-dimethylpiperazine; aromatic nitrogen compounds, such as 4-dimethylaminopyridine, N-methylimidazole, N-vinylimidazole or 1,2-dimethylimidazole; organic ammonium compounds, such as benzyltrimethylammonium hydroxide or alkoxylated tertiary amines; what are called "delayed action" catalysts, which are modifications of known metal or amine catalysts;
- rheology modifiers, especially thickeners, especially sheet silicates, such as bentonites, derivatives of castor oil, hydrogenated castor oil, polyamides, polyamide waxes, polyurethanes, urea compounds, fumed silicas, cellulose ethers or hydrophobically modified polyoxyethylenes;
- natural resins, fats or oils, such as rosin, shellac, linseed oil, castor oil or soybean oil;
- nonreactive polymers, especially homo- or copolymers of unsaturated monomers, especially from the group comprising ethylene, propylene, butylene, isobutylene, isoprene, vinyl acetate or alkyl (meth)acrylates, especially polyethylenes (PE), polypropylenes (PP), polyisobutylenes, ethylene/vinyl acetate copolymers (EVA) or atactic poly-α-olefins (APAO);

flame-retardant substances, especially the aluminum hydroxide or magnesium hydroxide fillers already mentioned, and also especially organic phosphoric acid esters, such as especially triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris (2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenylphosphate), bisphenol A bis(diphenylphosphate) or ammonium polyphosphates;

additives, especially wetting agents, leveling agents, defoamers, deaerators, stabilizers against oxidation, heat, light or UV radiation, or biocides; or further substances customarily used in moisture-curing compositions.

It may be advisable to chemically or physically dry certain substances before mixing them into the composition.

More particularly, the composition may, as well as the at least one compound of formula (I), comprise further latent curing agents, especially oxazolidines that do not conform to the formula (I), or polyaldimines.

In a preferred embodiment of the invention, the composition comprises a combination of compounds of the formula (I) and at least one polyaldimine.

The polyaldimine here is especially an odorless polyaldimine.

The polyaldimine preferably has the formula (V) or (VI)

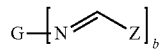
(V)

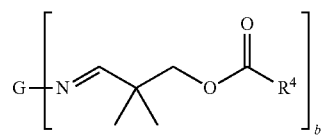
(VI)

where b is 2 or 3,

G is a b-valent aliphatic, cycloaliphatic or arylaliphatic hydrocarbyl radical optionally containing ether oxygen and having a molecular weight in the range from 28 to 6'000 g/mol, $R^4$ is an alkyl radical having 7 to 17 carbon atoms, especially a linear alkyl radical having 11 carbon atoms, and Z has the definitions already described.

Such a composition has particularly good storage stability and can be optimized to the mechanical demands for various applications. The composition is odorless as before and cures on contact with moisture.

In the case of use of polyaldimines of the formula (V), the composition shows a particularly low tendency to plasticizer migration.

In the case of use of polyaldimines of the formula (VI) in addition to the compound of the formula (I), the composition shows a lower tendency to plasticizer migration than if it had been cured without compound of the formula (I) with a correspondingly higher amount of polyaldimine of the formula (VI).

Preferably, G is a b-valent aliphatic, cycloaliphatic or arylaliphatic hydrocarbon radical having a molecular weight in the range from 45 to 500 g/mol.

More preferably, G is selected from the group consisting of 1,6-hexylene, (1,5,5-trimethylcyclohexan-1-yl)methane-1,3, 4(2)-methyl-1,3-cyclohexylene, 1,3-cyclohexylenebis (methylene), 1,4-cyclohexylenebis(methylene), 1,3-phenylenebis(methylene), 1,2-cyclohexylene, methylenedicyclohexan-4-yl, α,ω-polyoxypropylene with an average molecular weight in the range from 170 to 470 g/mol and trimethylolpropane- or glycerol-started tris(ω-polyoxypropylene) having an average molecular weight in the range from 330 to 450 g/mol.

In the composition, the ratio between the reactive groups releasable from the latent curing agents present, i.e. especially primary and secondary amino groups, hydroxyl groups and mercapto groups, and the isocyanate groups is preferably in the range from 0.1 to 1.9, more preferably in the range from 0.2 to 1.8.

For a composition free of aldimino groups, the ratio is preferably in the range from 0.5 to 1.8, especially 0.8 to 1.6.

For a composition containing aldimino groups as well, the ratio is preferably in the range from 0.2 to 1.5, especially 0.5 to 1.3.

The composition preferably contains a content of polyisocyanates and of polyurethane polymers containing isocyanate groups in the range from 5% to 90% by weight, especially 10% to 80% by weight.

The composition is especially produced with exclusion of moisture and stored at ambient temperature in moisture-tight containers. A suitable moisture-tight container especially consists of an optionally coated metal and/or plastic, and is especially a drum, a transport box, a hobbock, a bucket, a canister, a can, a bag, a tubular bag, a cartridge or a tube.

The composition may be in the form of a one-component composition or in the form of a multi-component, especially two-component, composition.

A composition referred to as a "one-component" composition is one in which all constituents of the composition are in the same container and which is storage-stable per se.

A composition referred to as a "two-component" composition is one in which the constituents of the composition are in two different components which are stored in separate containers and are not mixed with one another until shortly before or during the application of the composition.

The composition is preferably a one-component composition. Given suitable packaging and storage, it is storage-stable, typically over several months, up to one year or longer.

On application of the composition, the process of curing commences. This results in the cured composition.

In the case of a one-component composition, it is applied as such and then begins to cure under the influence of moisture or water. For acceleration of the curing, an accelerator component which contains or releases water and/or a catalyst can be mixed into the composition on application, or the composition, after application thereof, can be contacted with such an accelerator component.

In the case of a two-component composition, it is applied after the mixing of the two components and begins to cure by internal reaction, and the curing may be completed by the action of external moisture. The two components can be mixed continuously or batchwise with dynamic mixers or static mixers.

On curing, the isocyanate groups react under the influence of moisture with the amino and hydroxyl or mercapto groups released from the compound of the formula (I) and with any other blocked amino groups present. Some of the isocyanate groups, especially the excess isocyanate groups relative to the reactive groups released, react with one another under the influence of moisture and/or with any further reactive groups present in the composition.

The totality of these reactions of isocyanate groups that lead to the curing of the composition is also referred to as crosslinking.

The moisture required for the curing of the one-component composition preferably gets into the composition through diffusion from the air (atmospheric moisture). In the process, a solid layer of cured composition is formed on the surfaces of the composition which come into contact with air ("skin"). The curing continues in the direction of diffusion from the outside inward, the skin becoming increasingly thick and ultimately encompassing the entire composition applied. The moisture can also get into the composition additionally or entirely from one or more substrate(s) to which the composition has been applied and/or can come from an accelerator component which is mixed into the composition on application or is contacted therewith after application, for example by painting or spraying.

Any external moisture required to complete the curing of a two-component composition preferably comes from the air and/or from the substrates.

The composition is preferably applied at ambient temperature, especially in the range from about 0 to 50° C., preferably in the range from 5 to 40° C.

The composition is preferably likewise cured at ambient temperature.

The composition has a comparatively long open time.

The "open time" refers to the period of time over which the composition can be worked or reworked after the curing process has commenced.

The time until formation of a skin ("skin time") or until freedom from tack ("tack-free time") is a measure of the open time.

The crosslinking releases an aldehyde of the formula (IV). It is substantially nonvolatile and odorless and remains for the most part in the cured composition. It behaves or acts like a plasticizer therein. As such, it can in principle itself migrate and/or affect the migration of further plasticizers. The aldehyde of the formula (IV) has very good compatibility with the cured composition, barely migrates itself, and also does not trigger any enhanced migration of plasticizers.

The composition is preferably an adhesive or a sealant or a coating.

The adhesive or sealant or coating is preferably elastic.

The composition is especially suitable as an adhesive and/or sealant for bonding and sealing applications, especially in the construction and manufacturing industries or in motor vehicle construction, especially for parquet bonding, installable component bonding, cavity sealing, assembly, module bonding, vehicle body bonding, window pane bonding or joint sealing. Elastic bondings in motor vehicle construction are, for example, the bonded attachment of parts, such as plastic covers, trim strips, flanges, fenders, driver's cabins or other installable components, to the painted body of a motor vehicle, or the bonding of glass panes into the vehicle body, where the motor vehicles are especially automobiles, trucks, buses, rail vehicles or ships.

The composition is especially suitable as sealant for the elastic sealing of all kinds of joints, seams or cavities, especially of joints in construction, such as expansion joints or connection joints between structural components. A sealant having flexible properties is particularly suitable especially for the sealing of expansion joints in built structures.

As coating, the composition is suitable for the protection of floors or walls, especially as coating of balconies, terraces, open spaces, bridges, parking levels, or for the sealing of roofs, especially flat roofs or slightly inclined roof areas or roof gardens, or in the interior of buildings for water sealing, for example beneath tiles or flagstones in plumbing units or kitchens, or as floor covering in kitchens, industrial buildings or manufacturing spaces, or as seal in collection tanks, channels, shafts or wastewater treatment plants, or for the protection of surfaces as varnish or seal, or as casting compound for cavity sealing, as seam seal or as protective coating for pipes, for example.

It can also be used for repair purposes as seal or coating, for example of leaking roof membranes or floor coverings no longer fit for purpose, or especially as repair compound for highly reactive spray seals.

The composition can be formulated such that it has a pasty consistency with structurally viscous properties. A composition of this kind is applied by means of a suitable device, for example from commercial cartridges or kegs or hobbocks, for example in the form of a bead, which may have an essentially round or triangular cross-sectional area.

The composition can also be formulated such that it is fluid and "self-leveling" or only slightly thixotropic and can be poured out for application. As coating, it can, for example, subsequently be distributed flat up to the desired layer thickness, for example by means of a roller, a slide bar, a toothed applicator or a trowel. In one operation, typically a layer thickness in the range from 0.5 to 3 mm, especially 1.0 to 2.5 mm, is applied.

In one embodiment of the invention, the composition is a reactive hotmelt adhesive. For this purpose, preference is given to a polyurethane polymer which is solid at room temperature. A hotmelt adhesive is preferably applied in the molten state at a temperature in the range from 80 to 180° C.

A suitable compound of the formula (I) in a hotmelt adhesive composition is especially a compound of the formula (I a) having hydroxyl groups, which is used in such an amount that the ratio between the OH group and isocyanate groups present is in the range from 0.05 to 0.5. In this way, after the reaction between the OH groups and isocyanate groups, there are still sufficient free isocyanate groups present in order to react with the secondary amino groups released from the hydrolysis of the compound of the formula (I) and also with at least some of the OH groups released under crosslinking.

In addition, a compound of the formula (I d) is particularly suitable in a hotmelt adhesive composition, especially a diurethane.

The use of a compound of the formula (I) containing hydroxyl groups in a reactive hotmelt adhesive has various advantages. In the case of application of the adhesive in the molten state, typically at temperatures in the range from 80 to 180° C., blistering is suppressed, with the nonvolatility and odorlessness of the aldehyde released at these high temperatures constituting an enormous advantage, and the use of a compound of the formula (I a) having a hydroxyl group reduces the monomer content of the polyurethane polymer used through the reaction with the OH group.

In one embodiment of the invention, the composition is a primer. The compounds of the formula (I) generally exert a good adhesion-promoting effect, especially since the composition, after the curing, typically contains free hydroxyl groups that can interact with the substrate. The primer composition more preferably contains at least one compound of the formula (I b) which exerts a particularly good adhesion-promoting effect via its silane group.

The primer preferably contains at least one solvent. The primer optionally contains further constituents, especially catalysts, further silanes, titanates or zirconates, or optionally pigments, fillers, wetting agents, polyurethane polymers containing silane groups, or epoxy resins.

The primer is typically applied so as to leave, after the evaporation of the solvents, a closed film in a layer thickness in the region of a few micrometers to a few hundred micrometers on the substrate. It is typically used to improve the adhesion between a substrate and an adhesive and/or sealant or coating by allowing the primer film to develop adhesion both to the substrate and to the curable composition applied to the primer film.

The primer is typically applied to a substrate surface in a thin layer with a brush or roller. After a suitable waiting time during which the solvent partly or completely evaporates, the adhesive or sealant or coating is applied to the surface thus pretreated and typically has improved adhesion.

Such a primer preferably has a long open time, meaning that it exerts its adhesion-promoting effect over a long period after application. This makes it possible, for example, to market a component to be bonded with pre-applied primer (in "pre-primed" form) and to bond or join it at any later juncture without loss of adhesion. In this way, there is no need for primer application and hence for the handling of a typically solventborne product that requires safety devices such as vapor suction and protective clothing in the joining process, which constitutes a considerable advantage to many users.

Suitable substrates which can be bonded or sealed or coated with the composition are especially glass, glass ceramic, concrete, mortar, fiber cement, especially fiber cement boards, brick, tile, gypsum, especially gypsum boards, or natural stone, such as granite or marble;

repair or leveling compounds based on PCC (polymer-modified cement mortar) or ECC (epoxy resin-modified cement mortar);

metals or alloys, such as aluminum, copper, iron, steel, nonferrous metals, including surface-finished metals or alloys, such as zinc-plated or chromium-plated metals;

asphalt or bitumen;

leather, textiles, paper, wood, wood materials bonded with resins, such as phenolic, melamine or epoxy resins, resin/textile composites or further materials called polymer composites;

plastics, such as rigid and flexible PVC, polycarbonate, polystyrene, polyester, polyamide, PMMA, ABS, SAN, epoxy resins, phenolic resins, PUR, POM, TPO, PE, PP, EPM or EPDM, in each case untreated or surface-treated, for example by means of plasma, corona or flames;

fiber-reinforced plastics, such as carbon fiber-reinforced plastics (CFP), glass fiber-reinforced plastics (GFP) and sheet molding compounds (SMC);

insulation foams, especially made of EPS, XPS, PUR, PIR, rock wool, glass wool or foamed glass;

coated or painted substrates, especially painted tiles, coated concrete, powder-coated metals or alloys or painted metal sheets;

paints or varnishes, especially automotive topcoats.

If required, the substrates can be pretreated prior to application, especially by physical and/or chemical cleaning methods or the application of an activator or a primer.

It is possible to bond and/or seal two identical or two different substrates.

The application and curing of the composition affords an article bonded or sealed or coated with the composition. This article may be a built structure or a part thereof, especially a built structure in civil engineering above or below ground, a bridge, a roof, a staircase or a facade, or it may be an industrial good or a consumer good, especially a window, a pipe, a rotor blade of a wind turbine, a domestic appliance or a mode of transport, such as especially an automobile, a bus, a truck, a rail vehicle, a ship, an aircraft or a helicopter, or an installable component thereof.

The composition of the invention has advantageous properties. It is storage-stable with exclusion of moisture, even in the case of aromatic isocyanate groups. It has a sufficiently long open time to make possible a seamless distribution of the material applied or a positioning or readjustment of the objects bonded therewith over a certain period after application, which is important, for example, in the case of coatings over a large area or long sealing strips, or in the case of bonding of large or complex objects. Curing proceeds quickly, reliably, without blistering and without troublesome odor immissions, and so the composition can be used without limitation even under climatically unfavorable conditions, such as high air humidity and/or high temperature or with use of aqueous accelerator components. On curing, it rapidly builds up strength, the skin formed on the surface being really soon surprisingly nontacky and dry, which is very valuable especially in application on building sites, since contamination by, for example, dust is thereby prevented. The curing proceeds to completion and results in a high-quality material which combines a high mechanical strength and extensibility with a moderate modulus of elasticity and consequently is also suitable for flexible products. The cured composition is long-lived and especially very thermally stable. In spite of its content of released aldehyde of the formula (IV), the cured composition shows scarcely any defects caused by plasticizer migration, such as bleeding, discoloration, formation of specks, softening or substrate detachment, and can consequently be used without limitation even on porous substrates or on plastics which form stress cracks and in combination with outer layers.

The invention further provides for the use of at least one aldehyde of the formula (IV)

(IV)

as blocking agent for amino alcohols, in which the nitrogen atom and the oxygen atom are separated from one another by two or three carbon atoms, where Z has the definitions already given.

Preference is given here to using, as aldehyde of the formula (IV), a mixture comprising 4-decylbenzaldehydes, 4-undecylbenzaldehydes, 4-dodecylbenzaldehydes, 4-tridecylbenzaldehydes and 4-tetradecylbenzaldehydes, the alkyl radicals of which are mainly branched.

Preferably, the amino alcohols already mentioned are blocked.

This use affords oxazolidines or oxazinanes that have the advantageous properties already described.

EXAMPLES

Working examples are adduced hereinafter, which are intended to further elucidate the invention described. Of course, the invention is not limited to these described working examples.

Chemicals otherwise specified in the examples were purchased from Sigma-Aldrich or Merck (in purum or puriss. quality) and used as obtained. "Standard climatic conditions" ("SCC") refer to a temperature of 23±1° C. and a relative air humidity of 50±5%.

Aldehydes Used:

Aldehyde-1: Fractionated aldehyde mixture obtained from formylation, catalyzed by means of HF—BF$_3$, of C$_{10-14}$-alkylbenzene, containing mainly branched 4-(C$_{10-14}$-alkyl)benzaldehydes. (Average aldehyde equivalent weight 290 g/eq)

Benzaldehyde (106.1 g/mol)

Isobutyraldehyde (72.1 g/mol)

2,2-Dimethyl-3-lauroyloxypropanal (284.4 g/mol)

Aldehyde-1 is a mixture of aldehydes of the formula (IV).

Benzaldehyde and 2,2-dimethyl-3-lauroyloxypropanal do not conform to the formula (IV).

Production of Latent Curing Agents:

The amine value (including blocked amino groups) was determined by means of titration (with 0.1N HClO$_4$ in acetic acid versus crystal violet).

Viscosity was measured with a thermostated Rheotec RC30 cone-plate viscometer (cone diameter 50 mm, cone angle 1°, cone tip-plate distance 0.05 mm, shear rate 10 s$^{-1}$ for viscosities <150 Pa·s, shear rate 1 s$^{-1}$ for viscosities >150 Pa·s).

Infrared spectra (FT-IR) were measured as undiluted films on a Nicolet iS5 FT-IR instrument from Thermo Scientific equipped with a horizontal ATR measurement unit with a diamond crystal. The absorption bands are reported in wavenumbers (cm$^{-1}$).

Oxazolidine A-1:

To an initial charge of 63.09 g of diethanolamine in a round-bottom flask were added 178.09 g of aldehyde-1 and 0.50 g of salicylic acid, and the reaction mixture was stirred at 80° C. under reduced pressure until all the water had been removed. A yellowish liquid having an amine value of 141.6 mg KOH/g was obtained.

FT-IR: 2954, 2923, 2871, 2857, 1704, 1607, 1509, 1465, 1425, 1378, 1343, 1298, 1213, 1174, 1045, 1018, 937, 884, 825, 722.

The oxazolidine A-1 is a monooxazolidine and conforms to the formula (I a).

Oxazolidine A-2:

An initial charge of 37.80 g of oxazolidine A-1, prepared as described above, under a nitrogen atmosphere in a round-bottom flask was heated up. At 80° C., 8.33 g of hexamethylene 1,6-diisocyanate was added dropwise and then the mixture was stirred at 80° C. until no isocyanate groups were detectable any longer by means of IR spectroscopy. A highly viscous yellow oil that was liquid at room temperature and had a viscosity of 16.9 Pa·s at 60° C. and an amine value of 116.4 mg KOH/g was obtained. After a storage time of 18 months in a closed container, consistency and viscosity were unchanged.

FT-IR: 2955, 2923, 2853, 1704, 1634, 1532, 1463, 1376, 1352, 1242, 1213, 1178, 1105, 1057, 1019, 825, 772, 722.

The oxazolidine A-2 is a bisoxazolidine and conforms to the formula (I d).

Oxazolidine A-3:

To an initial charge of 44.50 g of polyoxypropylene having a terminal 2-hydroxypropylamino group at each end and an average molecular weight of about 350 g/mol (Jeffamine® C-346 from Huntsman) in a round-bottom flask were added 80.00 g of aldehyde-1 and 0.50 g of salicylic acid, and the reaction mixture was stirred at 80° C. under reduced pressure until all the water had been removed. A yellowish liquid having a viscosity of 1.1 Pa·s at 20° C. and an amine value of 111.8 mg KOH/g was obtained.

FT-IR: 2957, 2923, 2870, 2853, 1726, 1704, 1645, 1606, 1575, 1456, 1375, 1304, 1212, 1194, 1168, 1094, 1062, 1017, 826, 722.

The oxazolidine A-3 is a bisoxazolidine and conforms to the formula (I d).

Oxazolidine A-4:

To an initial charge of 29.79 g of N-(3-(2-methylphenyloxy)-2-hydroxy-1-propyl)propane-1,2-diamine, prepared as described hereinafter, in a round-bottom flask were added 80.00 g of aldehyde-1 and 0.50 g of salicylic acid, and the reaction mixture was stirred at 80° C. under reduced pressure until all the water had been removed. An orange liquid having a viscosity of 3.0 Pa·s at 20° C. and an amine value of 116.5 mg KOH/g was obtained.

FT-IR: 2955, 2923, 2870, 2853, 1704, 1645, 1605, 1495, 1461, 1378, 1304, 1245, 1213, 1168, 1122, 1051, 1018, 826, 748, 722.

The oxazolidine A-4 is an iminooxazolidine and conforms to the formula (I c).

N-(3-(2-methylphenyloxy)-2-hydroxy-1-propyl)propane-1,2-diamine was prepared by heating an initial charge of 4.74 kg of propane-1,2-diamine under a nitrogen atmosphere to 70° C. and then, with good stirring, gradually adding 2.93 kg of o-cresyl glycidyl ether (Araldite® DY-K, from Huntsman), in the course of which the temperature of the reaction mixture was 70 to 80° C. After 1 hour at 80° C., the reaction mixture was cooled down and propane-1,2-diamine and further volatile constituents were removed by distillation by means of a thin-film evaporator (0.5-1 mbar, jacket temperature 115° C.). What was obtained was a clear yellowish liquid having an amine value of 478.7 mg KOH/g and a viscosity of 3.3 Pa·s at 20° C.

Oxazolidine A-5:

To an initial charge of 35.05 g of N-(3-(2-methylphenyloxy)-2-hydroxy-1-propyl)-2(4)-methylpentane-1,5-diamine, prepared as described hereinafter, in a round-bottom flask were added 80.00 g of aldehyde-1 and 0.50 g of salicylic acid, and the reaction mixture was stirred at 80° C. under reduced pressure on a rotary evaporator until all the water had been removed. An orange liquid having a viscosity of 3.1 Pa·s at 20° C. and an amine value of 112.0 mg KOH/g was obtained.

FT-IR: 2955, 2923, 2870, 2853, 1704, 1647, 1605, 1495, 1461, 1377, 1304, 1245, 1168, 1122, 1051, 1038, 1018, 827, 748, 712.

The oxazolidine A-5 is an iminooxazolidine and conforms to the formula (I c).

N-(3-(2-methylphenyloxy)-2-hydroxy-1-propyl)-2(4)-methylpentane-1,5-diamine was prepared by heating an initial charge of 4.65 kg of 1,5-diamino-2-methylpentane (Dytek® A, from Invista) under a nitrogen atmosphere to 70° C. and then, with good stirring, gradually adding 1.83 kg of o-cresyl glycidyl ether (Araldite® DY-K, from Huntsman), in the course of which the temperature of the reaction mixture was 70 to 80° C. After 1 hour at 80° C., the reaction mixture was cooled down and 1,5-diamino-2-methylpentane and further volatile constituents were removed by distillation by means of a thin-film evaporator (0.5-1 mbar, jacket temperature 160° C.). What was obtained was a clear yellowish liquid having an amine value of 367.1 mg KOH/g and a viscosity of 6.5 Pa·s at 20° C.

Oxazolidine A-6:

An initial charge of 30.16 g of polyoxypropylenediamine having an average molecular weight of about 240 g/mol (Jeffamine® D-230 from Huntsman) in a round-bottom flask was heated up to 70° C. While stirring, 37.55 g of phenyl glycidyl ether was added gradually and then the mixture was stirred at 80° C. for 2 hours under a nitrogen atmosphere, forming a bis(α,β-hydroxylamine). To this reaction product were added 80.00 g of aldehyde-1 and 0.50 g of salicylic acid, and the reaction mixture was stirred at 80° C. under reduced pressure until all the water had been removed. A yellowish liquid having a viscosity of 3.5 Pa·s at 20° C. and an amine value of 100.9 mg KOH/g was obtained.

FT-IR: 2956, 2923, 2870, 2853, 1704, 1645, 1600, 1587, 1496, 1456, 1376, 1301, 1244, 1170, 1101, 1077, 1042, 1018, 827, 752, 690.

The oxazolidine A-6 is a bisoxazolidine and conforms to the formula (I d).

Oxazolidine A-7:

The procedure was as described for oxazolidine A-6, except that 250.00 g of a polyoxypropylenediamine having an average molecular weight of about 2'000 g/mol (Jeffamine® D-2000 by Huntsman) was used rather than the polyoxypropylenediamine having an average molecular weight of about 240 g/mol. An orange liquid having a viscosity of 1.8 Pa·s at 20° C. and an amine value of 31.3 mg KOH/g was obtained.

FT-IR: 2968, 2926, 2897, 2858, 1704, 1601, 1497, 1456, 1372, 1343, 1245, 1098, 1015, 925, 828, 753, 691.

The oxazolidine A-7 is a bisoxazolidine and conforms to the formula (I d).

Oxazolidine A-8:

To an initial charge of 16.97 g of methylpentanediol diacrylate (SR341, from Sartomer) in a round-bottom flask was added 9.16 g of ethanolamine, and the reaction mixture was heated up to 50° C. and stirred for 2 hours, forming a bis(α,β-hydroxylamine). To this reaction product were added 45.83 g of aldehyde-1 and 0.50 g of salicylic acid, and the reaction mixture was stirred at 80° C. under reduced pressure until all the water had been removed. A yellowish liquid having a viscosity of 1.6 Pa·s at 20° C. and an amine value of 121.0 mg KOH/g was obtained.

FT-IR: 2955, 2923, 2871, 2853, 1734, 1704, 1647, 1607, 1458, 1378, 1301, 1212, 1179, 1109, 1054, 1018, 826, 722.

The oxazolidine A-8 is a bisoxazolidine and conforms to the formula (I d).

Oxazinane A-9:

The procedure was as described for oxazolidine A-8, except that 11.27 g of 3-amino-1-propanol was used rather than ethanolamine. A yellowish liquid having a viscosity of 2.9 Pa·s at 20° C. and an amine value of 118.6 mg KOH/g was obtained.

FT-IR: 2954, 2923, 2853, 1734, 1705, 1461, 1378, 1305, 1177, 1157, 1117, 1079, 1051, 977, 924, 826, 781, 722.

The oxazinane A-9 is a bisoxazinane and conforms to the formula (I d).

Oxazolidine A-10:

To an initial charge of 5.21 g of N-(2-aminoethyl)ethanolamine in a round-bottom flask with a water separator (Dean-Stark apparatus) were added 30.56 g of aldehyde-1, 50 ml of cyclohexane and 0.10 g of salicylic acid, and the reaction mixture was boiled under reflux at 120° C. until all the water had separated out. Subsequently, the reaction mixture was cooled and filtered, and the volatile constituents were removed under reduced pressure on a rotary evaporator at 80° C. An orange liquid having a viscosity of 1.1 Pa·s at 20° C. and an amine value of 160.2 mg KOH/g was obtained.

FT-IR: 2955, 2920, 2852, 1705, 1647, 1608, 1572, 1457, 1377, 1343, 1301, 1220, 1174, 1138, 1060, 1018, 986, 962, 826, 722.

The oxazolidine A-10 is an iminooxazolidine and conforms to the formula (I c).

Aminal A-11:

To an initial charge of 11.62 g of N,N'-diethylethylenediamine in a round-bottom flask was added 32.01 g of aldehyde-1 while stirring. Thereafter, the reaction mixture was freed of the water of reaction at 80° C. under reduced pressure on a rotary evaporator. An orange liquid having a viscosity of 0.09 Pa·s at 20° C. and an amine value of 265.7 mg KOH/g was obtained.

FT-IR: 2957, 2924, 2871, 2853, 2792, 2525, 1706, 1607, 1508, 1465, 1423, 1377, 1340, 1280, 1226, 1164, 1055, 1019, 995, 958, 861, 824, 805, 722. The aminal A-11 conforms to the formula (I) where n is 1, X is $NR^O$, $R^O$ and A are each ethyl and Y is ethylene.

Aminal A-12:

To an initial charge of 24.04 g of N,N'-dibenzylethylenediamine in a round-bottom flask was added 32.01 g of aldehyde-1 while stirring. Thereafter, the reaction mixture was freed of the water of reaction at 80° C. under reduced pressure on a rotary evaporator. An orange liquid having a viscosity of 1.41 Pa·s at 20° C. and an amine value of 210.4 mg KOH/g was obtained.

FT-IR: 3085, 3062, 2954, 2923, 2870, 2852, 2792, 2722, 2520, 1804, 1705, 1605, 1507, 1453, 1423, 1377, 1338, 1295, 1248, 1212, 1153, 1120, 1072, 1028, 975, 911, 861, 827, 735, 690, 667.

The aminal A-12 conforms to the formula (I) where n is 1, X is $NR^O$, $R^O$ and A are each benzyl and Y is ethylene.

Oxazolidine A-13:

To an initial charge of 11.72 g of N-butylethanolamine in a round-bottom flask with a water separator (Dean-Stark apparatus) were added 29.68 g of aldehyde-1, 75 ml of cyclohexane and 0.10 g of salicylic acid, and the reaction mixture was boiled under reflux at 120° C. until all the water had separated out. Subsequently, the reaction mixture was cooled and filtered, and the volatile constituents were removed under reduced pressure on a rotary evaporator at 80° C. A yellowish liquid having a viscosity of 0.07 Pa·s at 20° C. and an amine value of 142.1 mg KOH/g was obtained.

FT-IR: 2955, 2921, 2854, 2800, 1706, 1614, 1576, 1464, 1426, 1377, 1341, 1296, 1217, 1178, 1152, 1067, 1019, 957, 925, 826, 741, 722.

The oxazolidine A-13 conforms to the formula (I a) where $A^1$ is n-butyl. It is especially suitable as a desiccant.

Oxazolidine A-14:

To an initial charge of 13.92 g (50 mmol) of 3-glycidoxypropyltriethoxysilane (Dynasylan® GLYEO, from Evonik) in a round-bottom flask was added 22.14 g (100 mmol) of 3-aminopropyltriethoxysilane (Dynasylan® AMEO, from Evonik), and the mixture was stirred at 70° C. until the epoxy groups had been converted. Subsequently, 30.56 g of aldehyde-1 was added and the reaction mixture was freed of the water of reaction at 80° C. under reduced pressure on a rotary evaporator. A pale orange liquid having a viscosity of 0.35 Pa·s at 20° C. and an amine value of 87.6 mg KOH/g was obtained.

FT-IR: 2957, 2924, 2854, 1705, 1647, 1607, 1573, 1508, 1456, 1389, 1343, 1297, 1166, 1102, 1076, 1017, 954, 827, 774.

The oxazolidine A-14 contains a mixture of oxazolidinosilane and aldiminosilane. The oxazolidinosilane conforms to the formula (I b) where $A^2$ is 3-triethoxysilylpropyl and Y is an ethylene radical 5-triethoxysilyl-2-oxapentyl-substituted in the alpha position to the oxazolidine oxygen. It is especially suitable as an adhesion promoter.

Oxazolidine B-1:

The procedure was as described for oxazolidine A-1, except that 64.95 g of benzaldehyde was used rather than aldehyde-1. A pale brown liquid having an amine value of 288.2 mg KOH/g was obtained.

Oxazolidine B-2:

An initial charge of 37.80 g of oxazolidine B-1, prepared as described above, under a nitrogen atmosphere in a round-bottom flask was heated up. At 80° C., 8.33 g of hexamethylene 1,6-diisocyanate was added dropwise and then the mixture was stirred at 80° C. until no isocyanate groups were detectable any longer by means of IR spectroscopy. What was obtained was a yellow material that was solid at room temperature and had an amine value of 181.4 mg KOH/g, which has a viscosity at 60° C. of 583.5 Pa·s.

Oxazolidine B-3:

The procedure was as described for oxazolidine A-3, except that 29.18 g of benzaldehyde was used rather than aldehyde-1. A pale brown liquid having a viscosity of 1.9 Pa·s at 20° C. and an amine value of 219.4 mg KOH/g was obtained.

Oxazolidine B-4:

The procedure was as described for oxazolidine A-4, except that 29.18 g of benzaldehyde was used rather than aldehyde-1. What was obtained was a viscous dark orange oil having a viscosity of 1'945 Pa·s at 20° C. and an amine value of 249.0 mg KOH/g, which gradually solidified over a few weeks when left to stand at room temperature.

Oxazolidine B-5:

The procedure was as described for oxazolidine A-5, except that 29.18 g of benzaldehyde was used rather than aldehyde-1. An orange oil having a viscosity of 93.5 Pa·s at 20° C. and an amine value of 226.0 mg KOH/g was obtained.

Oxazolidine B-6:

The procedure was as described for oxazolidine A-6, except that 29.18 g of benzaldehyde was used rather than aldehyde-1. An orange oil having a viscosity of 84.5 Pa·s at 20° C. and an amine value of 161.0 mg KOH/g was obtained.

Oxazolidine B-7:

The procedure was as described for oxazolidine A-7, except that 29.18 g of benzaldehyde was used rather than aldehyde-1. An orange liquid having a viscosity of 2.0 Pa·s at 20° C. and an amine value of 40.9 mg KOH/g was obtained.

Oxazolidine B-8:

The procedure was as described for oxazolidine A-8, except that 16.72 g of benzaldehyde was used rather than aldehyde-1. A yellowish liquid having a viscosity of 2.0 Pa·s at 20° C. and an amine value of 216.6 mg KOH/g was obtained.

Oxazinane B-9:

The procedure was as described for oxazolidine A-9, except that 16.72 g of benzaldehyde was used rather than aldehyde-1. A yellowish liquid having a viscosity of 10.5 Pa·s at 20° C. and an amine value of 205.1 mg KOH/g was obtained.

Oxazolidine B-10:

To an initial charge of 15.00 g of N-(2-aminoethyl) ethanolamine in a round-bottom flask with a water separator (Dean-Stark apparatus) were added 32.10 g of benzaldehyde, 50 ml of cyclohexane and 0.10 g of salicylic acid, and the reaction mixture was boiled under reflux at 120° C. until all the water had separated out. Subsequently, the reaction mixture was cooled and filtered, and the volatile constituents were removed under reduced pressure on a rotary evaporator at 80° C. An orange liquid having a viscosity of 0.83 Pa·s at 20° C. and an amine value of 385.1 mg KOH/g was obtained.

Oxazolidine L-1:

The procedure was as described for oxazolidine A-1, except that 174.65 g of 2,2-dimethyl-3-lauroyloxypropanal was used rather than aldehyde-1. A yellowish liquid having an amine value of 141.2 mg KOH/g was obtained.

Oxazolidine L-2:

An initial charge of 39.73 g of oxazolidine L-1, prepared as described above, under a nitrogen atmosphere in a round-bottom flask was heated up. At 80° C., 8.33 g of hexamethylene 1,6-diisocyanate was added dropwise and then the mixture was stirred at 80° C. until no isocyanate groups were detectable any longer by means of IR spectroscopy. A yellowish liquid having a viscosity of 6 Pa·s at 20° C. and an amine value of 115.2 mg KOH/g was obtained.

Oxazolidine IB-2: (Corresponding to Incozol 4, from Incorez)

An initial charge of 15.92 g of N-(2-hydroxyethyl)-2-isopropyloxazolidine (Incozol 3, from Incorez) under a nitrogen atmosphere in a round-bottom flask was heated up. At 80° C., 8.33 g of hexamethylene 1,6-diisocyanate was added dropwise and then the mixture was stirred at 80° C. until no isocyanate groups were detectable any longer by means of IR spectroscopy. What was obtained was a yellowish liquid having a viscosity of 36 Pa·s at 20° C. and an amine value of 220.0 mg KOH/g, which crystallized within a few weeks and had to be melted for further use.

Oxazolidine IB-10:

To an initial charge of 15.00 g of N-(2-aminoethyl) ethanolamine in a round-bottom flask with a water separator (Dean-Stark trap) were added 21.81 g of isobutyraldehyde, 50 ml of cyclohexane and 0.10 g of salicylic acid, and the reaction mixture was boiled under reflux at 120° C. until all the water had separated out. Subsequently, the reaction mixture was cooled and filtered, and the volatile constituents were removed under reduced pressure on a rotary evaporator at 80° C. A yellowish liquid having a viscosity of 0.01 Pa·s at 20° C. and an amine value of 521.7 mg KOH/g was obtained.

Incozol 2:

Monooxazolidine based on N-butylethanolamine and 2-ethylhexanal, from Incorez.

The oxazolidines A-1 to A-8, A-10, A-13 and A-14, the oxazinane A-9 and the aminals A-11 and A-12 are compounds of the formula (I).

The oxazolidines B-1 to B-8 and B-10, the oxazinane B-9 and the oxazolidines L-1, L-2, IB-2, IB-10 and Incozol 2 do not conform to the formula (I) and serve as comparison.

Aldimine C-1:

50.00 g of 2,2-dimethyl-3-lauroyloxypropanal were initially charged in a round-bottom flask under a nitrogen atmosphere. While stirring, 13.93 g of 3-aminomethyl-3,5,5-trimethylcyclohexylamine was added and then the volatile constituents were removed at 80° C. and a reduced pressure of 10 mbar. A pale-yellow odorless liquid having a viscosity of 0.2 Pa·s at 20° C. and an amine value of 153.0 mg KOH/g was obtained.

The aldimine A-1 is a dialdimine and conforms to the formula (VI).

Preparation of Polymers Containing Isocyanate Groups

Polymer P1:

400 g of polyoxypropylenediol (Acclaim® 4200, from Covestro; OH number 28.5 mg KOH/g) and 52 g of diphenylmethane 4,4'-diisocyanate (Desmodur® 44 MC L, from Covestro) were reacted by a known method at 80° C. to give an NCO-terminated polyurethane polymer which was liquid at room temperature and had a content of free isocyanate groups of 1.85% by weight.

Polymer P2:

590 g of polyoxypropylenediol (Acclaim® 4200, from Covestro; OH number 28.5 mg KOH/g), 1180 g of polyoxypropylene/polyoxyethylenetriol (Caradol® MD34-02, from Shell; OH number 35.0 mg KOH/g) and 230 g of isophorone diisocyanate (Vestanat® IPDI, from Evonik) were reacted by a known method at 80° C. to give an NCO-terminated polyurethane polymer which was liquid at room temperature and had a content of free isocyanate groups of 2.10% by weight.

Polymer P3:

356 g of polyoxypropylenediol (Acclaim® 4200, from Covestro; OH number 28.5 mg KOH/g), 100 g of polyoxypropylenetriol (Acclaim® 6300, from Covestro; OH number 28.0 mg KOH/g) and 40 g of a mixture of tolylene 2,4- and 2,6-diisocyanate in an 80/20 ratio (Desmodur® T 80, from Covestro) were reacted by a known method at 80° C. to give an NCO-terminated polyurethane polymer which was liquid at room temperature and had a content of free isocyanate groups of 1.80% by weight.

Polymer P4:

300.0 g of polyoxypropylene/polyoxyethylenediol (Desmophen® L300, from Covestro; OH number 190.0 mg KOH/g) and 228.8 g of isophorone diisocyanate (Vestanat® IPDI, from Evonik) were reacted by a known method at 60° C. to give an NCO-terminated polyurethane polymer which was liquid at room temperature and had a content of free isocyanate groups of 7.91% by weight.

Polymer P5:

1300 g of polyoxypropylenediol (Acclaim® 4200 N, from Covestro; OH number 28.5 mg KOH/g), 2600 g of polyoxypropylenetriol (Caradol® MD34-02, from Shell; OH number 35.0 mg KOH/g), 600 g of diphenylmethane 4,4'-diisocyanate (Desmodur® 44 MC L, from Covestro) and 500 g of diisodecyl phthalate (Palatinol® Z, BASF) were reacted at 80° C. to give an NCO-terminated polyurethane polymer having a content of free isocyanate groups of 2.05% by weight.

Polyurethane Compositions (One-Component)

Compositions Z1 to Z27:

For each composition, the ingredients specified in tables 1 to 2 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture. Each composition was tested as follows:

As a measure of storage stability, Viscosity (1d RT) was determined the day after production and Viscosity (7d 60° C.) after storage for 7 days in a closed container in a circulation oven at 60° C., as described above.

As a measure of the open time, Tack-free time was determined. For this purpose, a few grams of the composition were applied to cardboard in a layer thickness of about 2 mm and, under standard climatic conditions, the time until, when the surface of the composition was gently tapped by means of an LDPE pipette, there were for the first time no residues remaining any longer on the pipette was determined.

To determine the mechanical properties, each composition was poured onto a PTFE-coated film to give a film of thickness 2 mm and stored under standard climatic conditions for 7 days, and a few dumbbells having a length of 75 mm with a bar length of 30 mm and a bar width of 4 mm were punched out of the film and these were tested in accordance with DIN EN 53504 at a pull rate of 200 mm/minute for Tensile strength (breaking force), Elongation at break, Modulus of elasticity 5% (at 0.5%-5% elongation) and Modulus of elasticity 50% (at 0.5%-50% elongation).

Appearance was assessed visually on the films produced. "Nice" was used to describe a clear film with a nontacky surface without blisters.

Odor was assessed by smelling by nose at a distance of 2 cm from the freshly produced films. "Yes" means that an odor was clearly perceptible. "No" means that no odor was perceptible.

The results are reported in tables 1 to 2.

The compositions labeled with (Ref) are comparative examples.

TABLE 1

Composition (in parts by weight) and properties of Z1 to Z13.

| Composition | Z1 | Z2 (Ref) | Z3 (Ref) | Z4 (Ref) | Z5 | Z6 (Ref) |
|---|---|---|---|---|---|---|
| Polymer P1 | 50.00 | 50.00 | 50.00 | 50.00 | 50.00 | 50.00 |
| Oxazolidine | A-2 | B-2 | L-2 | IB-2 | A-3 | B-3 |
|  | 8.48 | 5.44 | 8.57 | 4.49 | 5.80 | 2.95 |
| Salicylic acid solution[1] | 1.00 | 1.00 | 1.00 | 1.00 | 1.00 | 1.00 |
| DBTDL solution[2] | 0.10 | 0.10 | 0.10 | 0.10 | 0.10 | 0.10 |
| Viscosity [Pa · s] 20° C. |  |  |  |  |  |  |
| (1 d RT) | 53 | 62 | 41 | 51 | 95 | 113 |
| (7 d 60° C.) | 96 | 125 | 45 | gelated | 134 | 178 |
| Tack-free time | 50' | 70' | 10 h | 15' | 40' | 50' |
| Tensile strength [MPa] | 1.02 | 0.99 | 0.63 | 1.56 | 0.67 | 0.78 |
| Elongation at break [%] | 131 | 125 | 95 | 182 | 71 | 82 |
| Modulus of elasticity 5% [MPa] | 1.55 | 1.61 | 1.10 | 2.12 | 1.37 | 1.50 |
| Modulus of elasticity 50% | 0.96 | 1.01 | 0.65 | 1.29 | 0.92 | 1.00 |
| Appearance | nice | nice | tacky, fine blisters | nice | nice | nice |
| Odor | no | yes | no | yes | no | yes |

TABLE 1-continued

Composition (in parts by weight) and properties of Z1 to Z13.

| Composition | Z7 | Z8 (Ref) | Z9 | Z10 (Ref) | Z11 | Z12 | Z13 |
|---|---|---|---|---|---|---|---|
| Polymer P1 | 50.00 | 50.00 | 50.00 | 50.00 | 50.00 | 50.00 | 50.00 |
| Oxazolidine | A-4 | B-4 | A-5 | B-5 | A-6 | A-8 | Oxazinane A-9 |
|  | 8.48 | 3.97 | 8.82 | 4.37 | 6.42 | 5.35 | 5.46 |
| Salicylic acid solution[1] | 1.00 | 1.00 | 1.00 | 1.00 | 1.00 | 1.00 | 1.00 |
| DBTDL solution[2] | 0.10 | 0.10 | 0.10 | 0.10 | 0.10 | 0.10 | 0.10 |
| Viscosity [Pa · s] 20° C. | | | | | | | |
| (1 d RT) | 47 | 61 | 44 | 61 | 75 | 43 | 45 |
| (7 d 60° C.) | 80 | 90 | 72 | 77 | 116 | 133 | 108 |
| Tack-free time | 165' | 120' | 95' | 55' | 55' | 85' | 180' |
| Tensile strength [MPa] | 0.47 | 0.88 | 0.58 | 0.80 | 0.63 | 0.66 | 0.62 |
| Elongation at break [%] | 283 | 334 | 214 | 303 | 99 | 83 | 85 |
| Modulus of elasticity 5% [MPa] | 0.41 | 0.45 | 0.76 | 0.91 | 1.05 | 1.21 | 1.05 |
| Modulus of elasticity 50% | 0.20 | 0.25 | 0.43 | 0.51 | 0.69 | 0.80 | 0.72 |
| Appearance | nice | nice | nice | nice | nice | nice | nice |
| Odor | no | yes | no | yes | no | no | no |

[1]5% in dioctyl adipate
[2]5% dibutyltin dilaurate in diisodecyl phthalate

TABLE 2

Composition (in parts by weight) and properties of Z14 to Z27.

| Composition | Z14 | Z15 (Ref) | Z16 (Ref) | Z17 | Z18 (Ref) |
|---|---|---|---|---|---|
| Polymer P2 | 50.00 | 50.00 | 50.00 | 50.00 | 50.00 |
| Oxazolidine | A-2 | B-2 | IB-2 | A-4 | B-4 |
|  | 9.64 | 6.19 | 5.10 | 9.64 | 4.51 |
| Salicylic acid solution[1] | 1.00 | 1.00 | 1.00 | 1.00 | 1.00 |
| DBTDL solution[2] | 0.50 | 0.50 | 0.50 | 0.50 | 0.50 |
| Viscosity [Pa · s] 20° C. | | | | | |
| (1 d RT) | 30 | 38 | 23 | 14 | 32 |
| (7 d 60° C.) | 83 | 133 | 89 | 26 | 45 |
| Tack-free time | 20' | 30' | 15' | 240' | 170' |
| Tensile strength [MPa] | 0.85 | 1.09 | 1.11 | 0.54 | 0.82 |
| Elongation at break [%] | 136 | 136 | 110 | 131 | 177 |
| Modulus of elasticity 5% [MPa] | 1.04 | 1.63 | 1.80 | 0.63 | 0.87 |
| Modulus of elasticity 50% | 0.72 | 1.04 | 1.20 | 0.45 | 0.60 |
| Appearance | nice | nice | nice | nice | nice |
| Odor | no | yes | yes | no | yes |

| Composition | Z19 | Z20 (Ref) | Z21 | Z22 |
|---|---|---|---|---|
| Polymer P2 | 50.00 | 50.00 | 50.00 | 50.00 |
| Oxazinane | A-5 | B-5 | A-8 | Oxazolidine A-9 |
|  | 10.02 | 4.96 | 6.09 | 6.21 |
| Salicylic acid solution[1] | 1.00 | 1.00 | 1.00 | 1.00 |
| DBTDL solution[2] | 0.50 | 0.50 | 0.50 | 0.50 |
| Viscosity [Pa · s] 20° C. | | | | |
| (1 d RT) | 18 | 27 | 18 | 18 |
| (7 d 60° C.) | 26 | 37 | 85 | 33 |
| Tack-free time | 100' | 75' | 70' | 165' |
| Tensile strength [MPa] | 0.63 | 0.80 | 0.68 | 0.44 |
| Elongation at break [%] | 145 | 137 | 77 | 107 |
| Modulus of elasticity 5% [MPa] | 0.72 | 1.04 | 1.19 | 0.72 |
| Modulus of elasticity 50% | 0.49 | 0.72 | 0.87 | 0.44 |
| Appearance | nice | nice | nice | nice |
| Odor | no | yes | no | no |

TABLE 2-continued

Composition (in parts by weight) and properties of Z14 to Z27.

| Composition | Z23 | Z24 (Ref) | Z25 (Ref) | Z26 | Z27 |
|---|---|---|---|---|---|
| Polymer P2 $_{IS-21}$ | 50.00 | 50.00 | 50.00 | 50.00 | 50.00 |
| Oxazolidine | A-10 | B-10 | IB-10 | Aminal A-11 | Aminal A-12 |
|  | 7.01 | 2.91 | 2.15 | 3.71 | 4.70 |
| Salicylic acid solution[1] | 1.00 | 1.00 | 1.00 | 1.00 | 1.00 |
| DBTDL solution[2] | 0.50 | 0.50 | 0.50 | 0.50 | 0.50 |
| Viscosity [Pa · s] 20° C. | | | | | |
| (1 d RT) | 18 | 24 | 23 | 23 | 17 |
| (7 d 60° C.) | 53 | 70 | 309 | 37 | 40 |
| Tack-free time | 50' | 35' | 15' | 275' | about 15 h |
| Tensile strength [MPa] | 0.69 | 0.90 | 1.03 | 0.92 | 0.82 |
| Elongation at break [%] | 77 | 79 | 97 | 202 | 201 |
| Modulus of elasticity 5% [MPa] | 1.27 | 1.72 | 1.77 | 0.91 | 0.79 |
| Modulus of elasticity 50% | 0.87 | 1.16 | 1.18 | 0.63 | 0.56 |
| Appearance | nice | nice | nice | nice | nice |
| Odor | no | yes | yes | no | no |

[1]5% in dioctyl adipate
[2]5% dibutyltin dilaurate in diisodecyl phthalate

Compositions Z28 to Z32:

For each composition, the ingredients specified in table 3 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture.

The Premixture-1 used was produced by mixing 24.0 parts by weight of Polymer P3, 2.5 parts by weight of diisodecyl phthalate, 40.8 parts by weight of chalk, 28 parts by weight of thickener, 4.5 parts by weight of titanium dioxide and 0.2 part by weight of p-tosyl isocyanate with exclusion of moisture by means of the centrifugal mixer and stored with exclusion of moisture.

The thickener was produced beforehand by gently heating an initial charge of 300 g of diisodecyl phthalate and 48 g of diphenylmethane 4,4'-diisocyanate (Desmodur® 44 MC L, from Covestro) in a vacuum mixer and then slowly adding 27 g of monobutylamine dropwise while stirring vigorously. The resultant paste was stirred for a further hour under reduced pressure while cooling.

Each composition was tested as described for composition Z1.

The results are reported in table 3.

The compositions labeled with (Ref) are comparative examples.

TABLE 3

Composition (in parts by weight) and properties of Z28 to Z32.

| Composition | Z28 | Z29 | Z30 | Z31 | Z32 (Ref) |
|---|---|---|---|---|---|
| Premixture-1 | 80.00 | 80.00 | 80.00 | 80.00 | 80.00 |
| Oxazolidine | A-4 | A-5 | A-6 | A-7 | — |
|  | 2.69 | 2.81 | 1.34 | 4.30 |  |
| Aldimine C-1 | — | — | 1.47 | 1.47 | 2.05 |
| Salicylic acid solution[1] | 0.40 | 0.40 | 0.40 | 0.40 | 0.40 |
| DBTDL solution[2] | 0.10 | 0.10 | 0.10 | 0.10 | 0.10 |
| Viscosity [Pa · s] 20° C. (1 d RT) | 118 | 110 | 160 | 101 | 168 |
| Tack-free time | 100' | 75' | 35' | 40' | 25' |
| Tensile strength [MPa] | 1.43 | 1.51 | 1.40 | 1.04 | 1.70 |
| Elongation at break [%] | 797 | 845 | 858 | 938 | 823 |
| Modulus of elasticity 5% [MPa] | 1.13 | 1.13 | 1.02 | 0.75 | 1.43 |
| Modulus of elasticity 50% | 0.60 | 0.65 | 0.54 | 0.41 | 0.67 |
| Appearance | nice | nice | nice | nice | nice |
| Odor | no | no | no | no | no |

[1]5% in dioctyl adipate
[2]5% dibutyltin dilaurate in diisodecyl phthalate

Compositions Z33 to Z36:

For each composition, the ingredients specified in table 4 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture.

Each composition was tested as follows:

As a measure of plasticizer migration, speck formation on cardboard was determined. For this purpose, each composition was applied to a piece of cardboard such that it had a round base area of diameter 15 mm and a height of 4 mm, and was stored under standard climatic conditions for 7 days. Around each composition, thereafter, a dark oval speck had formed on the cardboard. The dimensions thereof (height and width) were measured and reported in table 4 as Migration.

The compositions labeled with (Ref) are comparative examples.

TABLE 4

Composition (in parts by weight) and properties of Z33 to Z36.

| Composition | Z33 | Z34 (Ref) | Z35 (Ref) | Z36 (Ref) |
|---|---|---|---|---|
| Polymer P4 | 15.00 | 15.00 | 15.00 | 15.00 |
| Chalk | 15.00 | 15.00 | 15.00 | 15.00 |
| Silica | 1.13 | 1.13 | 1.13 | 1.13 |
| Curing agent | Oxazolidine A-2 | Oxazolidine B-2 | Aldimine C-1 | — |
|  | 7.65 | 4.61 | 5.46 |  |
| Salicylic acid solution[1] | 3.00 | 3.00 | 3.00 | 3.00 |
| DBTDL solution[2] | 1.50 | 1.50 | 1.50 | 1.50 |

TABLE 4-continued

Composition (in parts by weight) and properties of Z33 to Z36.

| Composition | Z33 | Z34 (Ref) | Z35 (Ref) | Z36 (Ref) |
|---|---|---|---|---|
| Migration Height (7 d) [mm] Width | 20 | 19 | 33 | 19 |
|  | 21 | 19 | 28 | 19 |
| Odor | no | yes | no | no |

[1]5% in dioctyl adipate
[2]5% dibutyltin dilaurate in diisodecyl phthalate

Use of Oxazolidine A-13 as Desiccant and/or Curing Agent:

Compositions Z37 to Z40:

For each composition, 105.0 parts by weight of Polymer P5, 60.0 parts by weight of the thickener described for composition Z28, 30.0 parts by weight of diisodecyl phthalate, 100.0 parts by weight of chalk, 7.0 parts by weight of silica (Aerosil® R972, from Evonik), the parts by weight of oxazolidine A-13 or Incozol 2 (from Incorez) specified in table 5, and 2.0 parts by weight of salicylic acid solution (5% by weight in dioctyl adipate) and 1.0 part by weight of DBTDL solution (5% by weight of dibutyltin dilaurate in diisodecyl phthalate) were mixed with exclusion of moisture by means of the centrifugal mixer and stored with exclusion of moisture.

The compositions were tested as follows:

As a measure of storage stability, Viscosity (1d RT) was determined the day after production, Viscosity (7d RT) after storage for 7 days in a closed container at room temperature, and Viscosity (7d 60° C.) after storage for 7 days in a closed container in a circulation oven at 60° C., as described above.

As a measure of the open time, Tack-free time was determined as described above.

The mechanical properties of Tensile strength (breaking strength), Elongation at break, and Modulus of elasticity 5% (at 0.5-5% elongation) and Modulus of elasticity 25% (at 0.5-25% elongation) were determined as described above.

Shore A hardness was determined according to DIN 53505 on test specimens cured under standard conditions for 7 days.

The results are reported in table 5.

The compositions labeled with (Ref) are comparative examples.

TABLE 5

Composition (in parts by weight) and properties of Z37 to Z40. "pbw" stands for parts by weight

| Composition | Z37 with 2.7 pbw of oxazolidine A13 | Z38 (Ref) with 1.6 pbw of Incozol 2 | Z39 with 7.5 pbw of oxazolidine A13 | Z40 (Ref) with 4.4 pbw of Incozol 2 |
|---|---|---|---|---|
| Viscosity [Pa · s] 20° C. |  |  |  |  |
| (1 d RT) | 152 | 168 | 141 | 159 |
| (7 d RT) | 161 | 171 | 144 | 218 |
| (7 d 60° C.) | 188 | 264 | 189 | 516 |
| Tack-free time | 120' | 75' | 150' | 80' |
| Tensile strength [MPa] | 1.75 | 1.84 | 1.79 | 1.95 |
| Elongation at break [%] | 420 | 400 | 940 | 875 |

TABLE 5-continued

Composition (in parts by weight) and properties of Z37 to Z40. "pbw" stands for parts by weight

| Composition | Z37 with 2.7 pbw of oxazolidine A13 | Z38 (Ref) with 1.6 pbw of Incozol 2 | Z39 with 7.5 pbw of oxazolidine A13 | Z40 (Ref) with 4.4 pbw of Incozol 2 |
|---|---|---|---|---|
| Modulus of elasticity 5% [MPa] | 3.66 | 3.65 | 1.44 | 1.63 |
| Modulus of elasticity 25% | 2.58 | 2.61 | 1.19 | 1.39 |
| Shore A | 53 | 56 | 31 | 35 |

Use of oxazolidine A-14 as adhesion promoter:
Activator-1:
2.5 g of oxazolidine A-14 were dissolved in 250 g of dry ethyl acetate and stored with exclusion of moisture.
Composition Z-41:
1.5 g of oxazolidine A-14 were mixed under a nitrogen atmosphere with 150 g of polymer P1 and stored with exclusion of moisture.

As a measure of action as adhesion promoter, spacer tape was applied longitudinally to a glass plate (float glass; from Rocholl, Schönbrunn, Germany) having dimensions of 10×15 cm on the air side so as to give three glass strips each of 2×8 cm. The first and second strips were each wiped once with an ethyl acetate-soaked hygiene wipe. The third strip was wiped once with a hygiene wipe wetted with activator-1. Subsequently, the glass plate treated in this way was stored under standard climatic conditions for flashoff for 2 h. Then 6 g of polymer P1 was applied in a layer thickness of about 3 mm to each of the first and third strips. 6 g of composition Z-41 was applied to the second strip in a layer thickness of about 3 mm.

The glass plate thus coated was stored under standard climatic conditions for 7 days and then attempts were made to detach the cured polymer films from the glass plate. The bonding was described as "very good" when the cured polymer could not be removed from the glass substrate. (Even after several cuts transverse to the strip direction down to the glass substrate, by which the polymer was cut away from the glass, and pulling the polymer strip away vertically, it was not possible to detach the polymer from the glass substrate.) The bonding was described as "none" when the cured polymer could be fully detached from the glass substrate.

The results are shown in table 6.

TABLE 6

| Pretreatment | Polymer strip | Bonding |
|---|---|---|
| Ethyl acetate | Polymer P1 | none |
| Ethyl acetate | Composition Z-41 | very good |
| Activator-1 | Polymer P1 | very good |

Primer Compositions Z-42:
125.0 g of Sika® Primer-209 N (pigmented primer containing isocyanate groups, from Sika Schweiz AG) was mixed with 21.2 g of oxazolidine A-14 and stored with exclusion of moisture.
Primer composition Z 42 was used as adhesion promoter on glass: a long flashoff time of 24 hours or 7 days was followed by application of Sikaflex®-250 DM-5 (one-component moisture-curing polyurethane adhesive, from Sika Switzerland AG) and curing thereof, and then the bonding thereof was tested. The reference used was Sika® Primer-209 N.

For each test, a glass plate was cleaned with isopropanol, wiped with a hygiene wipe soaked with Sika® Aktivator-100 (adhesion-promoting cleaner, from Sika Schweiz AG) and, after a flashoff time of 10 min, the primer composition was applied in a thin layer with a sponge. After a flashoff time of 24 hours or 7 days under standard climatic conditions, Sikaflex®-250 DM-5 that had been preheated to 60° C. was applied in the form of a triangular bead of width 10 mm and length 100 mm to the primer layer and the glass plate was stored under standard climatic conditions for 7 days, in the course of which the adhesive applied cured. Subsequently, the bonding of the adhesive bead on the glass plate was tested by making an incision into the bead at the end just above the bonding surface, holding the cut end of the bead with rounded tweezers and trying to pull the bead away from the substrate. Then the bead was incised again down to the substrate, the part of the bead that had been cut away was rolled up with the rounded tweezers and an attempt was again made to pull the bead away from the substrate. In this way, the bead was cut away from the substrate by pulling over a length of 80 mm. Subsequently, bonding was assessed with reference to the failure profile using the following scale:
1 (=very good) represents more than 95% cohesive failure
2 (=good) represents 75% to 95% cohesive failure
The results are reported in table 7.

TABLE 7

| Primer composition: | | Z-42 | Sika® Primer-209 N |
|---|---|---|---|
| Bonding of Sikaflex® 250 DM-5 | Flashoff time: | | |
| | 24 h | 1 | 2 |
| | 7 d | 1 | 1 |

The invention claimed is:
1. A composition comprising
at least one compound of formula (I) and
at least one polyisocyanate and/or at least one polyurethane polymer containing isocyanate groups; wherein the least one compound of the formula (I) is

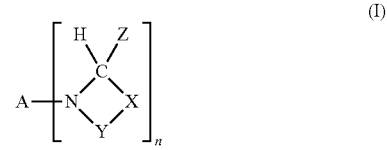

(I)

where
n is 1, 2 or 3,
Z is an aryl radical substituted by an alkyl or alkoxy group and having a total of 12 to 26 carbon atoms,
A is an n-valent organic radical having a molecular weight in the range from 15 to 10,000 g/mol,
X is O or S or $NR^o$ where $R^o$ is a monovalent organic radical having 1 to 18 carbon atoms, and
Y is a 1,2-ethylene or 1,3-propylene radical which is optionally substituted, where A and Y in the case that n =1 may also be bonded to a trivalent radical having 4 to 10 carbon atoms.

2. The composition as claimed in claim 1, wherein it is an adhesive or a sealant or a coating.

3. The composition as claimed in claim 1, wherein the composition is odorless.

4. The composition as claimed in claim 1, wherein the at least one compound of formula (I) is obtained from a reaction of at least one amine of the formula (III) with at least one aldehyde of the formula (IV)

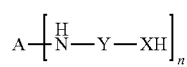 (III)

 (IV)

in a condensation reaction with removal of water, where A, n, X, Y and Z have the same definitions as provided above.

5. The composition as claimed in claim 1, wherein Z is the aryl radical substituted by an alkyl group and having a total of 12 to 26 carbon atoms.

6. The composition as claimed in claim 1, wherein Z is a radical of the formula (II)

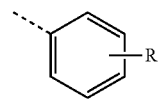 (II)

where R is a branched alkyl radical having 8 to 12 carbon atoms.

* * * * *